ature Patent [19]

United States Patent [19]

Nussbaum et al.

[11] 4,390,474
[45] Jun. 28, 1983

[54] SULFONATION PETROLEUM COMPOSITION

[75] Inventors: Marvin L. Nussbaum, Skokie; Edward A. Knaggs, Deerfield, both of Ill.

[73] Assignee: Stepan Chemical Company, Northfield, Ill.

[21] Appl. No.: 158,985

[22] Filed: Jun. 12, 1980

Related U.S. Application Data

[60] Continuation of Ser. No. 886,344, Mar. 13, 1978, abandoned, which is a division of Ser. No. 676,470, Apr. 13, 1976, Pat. No. 4,148,821, which is a continuation-in-part of Ser. No. 515,013, Oct. 16, 1974, abandoned, which is a continuation-in-part of Ser. No. 432,439, Jan. 11, 1974, abandoned, which is a continuation-in-part of Ser. No. 9,065, Feb. 5, 1970, abandoned.

[51] Int. Cl.$^3$ ................... C07C 143/24; C09K 3/00
[52] U.S. Cl. ........................ 260/505 R; 260/505 S; 252/8.55 D
[58] Field of Search .................... 260/505 S, 505 R

[56] References Cited

U.S. PATENT DOCUMENTS

| | | | |
|---|---|---|---|
| 2,285,390 | 6/1942 | Brandt | 260/505 S |
| 2,742,435 | 4/1956 | Korpi et al. | 260/505 S |
| 2,802,866 | 8/1957 | Salzmann et al. | 260/505 S |
| 3,007,961 | 11/1961 | Conwell et al. | 260/505 S |
| 3,042,713 | 7/1962 | Schar | 260/505 S |
| 3,215,628 | 11/1965 | Peacock | 260/505 S |
| 3,270,038 | 8/1966 | Marshall et al. | 260/505 S |
| 3,591,498 | 7/1971 | Benbury et al. | 260/505 S |
| 3,971,815 | 7/1976 | Sagel et al. | 260/505 S |

Primary Examiner—Alan Siegel
Attorney, Agent, or Firm—Hill, Van Santen, Steadman, Chiara & Simpson

[57] ABSTRACT

A technique for sulfonating petroleum oil feed stocks which materially increases the extent of reaction between the sulfonatable components present in the feed stock and sulfur trioxide, and yields an improved sulfonated product. The invention provides a method which includes forming a liquid mixture of a petroleum oil feed stock and an organic additive, feeding such mixture to a reaction zone, and contacting the mixure with a reactable sulfur trioxide material. The additive appears to promote continuity of materials during the reaction in such a way that substantially homogeneous product compositions are obtained. The invention also includes the so-attained reaction products. Methods of neutralizing, digesting, purifying and other treatments to improve product utility are taught.

42 Claims, No Drawings

SULFONATION PETROLEUM COMPOSITION

This is a continuation of application Ser. No. 886,344 filed Mar. 13, 1978 now abandoned which is a division of application Ser. No. 676,470 filed Apr. 13, 1976, now U.S. Pat. No. 4,148,821; which is continuation-in-part of Ser. No. 515,013 filed Oct. 16, 1974 (now abandoned); which in turn is a continuation-in-part application of our Ser. No. 432,439 filed Jan. 11, 1974 (now abandoned), which in turn is a continuation-in-part application of our Ser. No. 9,065 filed Feb. 5, 1970 (now abandoned), all of which are incorporated herein by reference.

BACKGROUND OF THE INVENTION

1. Field of the Invention

The invention relates to a method of sulfonating and somewhat more particularly to a method of sulfonating or sulfating petroleum feed stocks which promotes a high yield of petroleum sulfonates and to the resultant products.

2. Prior Art

A great number of processes have been advanced in this art in attempts to efficiently and economically provide petroleum sulfonates. These usually involve a batch process operation and/or an incremental treatment (quasi-continuous) of various oil feed stocks with concentrated sulfuric acid, oleum or other sulfonating agent with generally a very low yield of desired sulfonated product per contact and relatively large amounts of unwanted reaction by-products. (For a general discussion of the state of the art, see Industrial and Engineering Chemistry, Gilbert et al, Vol. 49, No. 1, January 1957, pages 31–38.)

Many batch processes involve the use of relatively high concentrations of solvents or diluents for achieving a somewhat homogeneous distribution of reactants within the batch and/or the use of multiple contact sequences with progressively increasing severity of sulfonation conditions. This usually involves increased costs since solvents and the like must be recovered, and higher temperatures, longer contact time, increased process costs, etc. In order to increase productivity rates and lower process costs and manpower expenditures, attempts have been made to continuously sulfonate petroleum oils. However, while it is possible to sulfonate a small fraction of the sulfonatable or sulfatable components present in various petroleum oils, attempts to raise the yield, or to increase the extent of reaction, for example, to that hypothetically possible, have been unsuccessful, particularly on the basis of a single cycle or contact.

A special problem has been found in attempting to sulfonate petroleum and/or fractions thereof (both of which, as is well known, typically comprise a complex mixture of various organic materials), in contradistinction to readily sulfonatable chemicals which are of relatively uniform composition, such as dodecylbenzene, ethoxylated alcohols, etc. When one attempts to drive a sulfonation reaction to completion with petroleum oils, such as by adding increased amounts of sulfur trioxide approaching a mol-for-mol basis, based on the sulfonatable components present in a petroleum oil, charring, oxidation, sludge formation and/or substantial polysulfonation occur in the reaction vessel, such as in a tubular reaction vessel, to the point where the vessel becomes plugged and continuous processing becomes impractical or impossible. Even in instances where the reaction vessel remains functional, the resultant reaction product is either of only limited utility or must be further purified or treated to remove solid-like particles therein and render at least some portion of the reaction product useful as a liquid. As an example, when one attempts to sulfonate a petroleum oil containing, say, about 40 to 45% by weight of sulfonatable components, in general, the best that one can achieve with heretofore available processes is a yield of about 10% sulfonated materials, or roughly a 25% conversion.

Typically, petroleum sulfonates heretofore available comprised by-product mahogany sulfonates which are produced by treating petroleum lubricating raffinates or other petroleum fractions with oleum ($SO_3$ dissolved in sulfuric acid) under controlled time-temperature conditions so that the aromatic portion of the lubricant stock forms by-product organic sulfonates (oil-soluble mahogany acids and water-soluble oil insoluble green acids), leaving mineral white oil, which is recovered after removal of the sulfonates. Additional details for white mineral oil manufacture may be found in Erich Meyer "White Mineral Oil and Petrolatum and Their Related Products" (Chemical Publishing Co., Inc., New York) 1968. The organic sulfonates so produced contain appreciable quantities of "sludge", generally comprised of viscous water-soluble (oil insoluble) organic sulfonates which are a mixture of polysulfonates and low equivalent weight monosulfonates. This sludge must be removed from the mahogany sulfonates before a commercially acceptable product can be obtained. However, typical green acid "sludge" yields are manyfold greater than oil-soluble mahogany sulfonates.

SUMMARY OF THE INVENTION

There has now been discovered a new technique by which petroleum oil feed stocks can be sulfonated with $SO_3$ in admixture with an additive so as to produce a substantially homogeneous liquid product which not only has a high content of sulfonated material but also has a high total and controllable percentage of monosulfonated components and a greatly reduced amount of polysulfonates. The technique can be practice without the charring, oxidation and severe polysulfonation problems experienced in the prior art when petroleum oil feed stocks are directly sulfonated with $SO_3$ so as to produce as a primary product the desired sulfonation reaction material directly, as opposed to low yielding secondary methods, such as in mahogany sulfonate production.

The sulfonated products of the present invention, without further refining, are particularly well suited for use in micellar systems adapted for employment in oil recovery, particularly in enhanced or tertiary oil recovery.

In one aspect, the present invention provides an improved method for sulfonating various petroleum oil feed stocks with $SO_3$. This method offers the capability of overcoming all or substantially all of the above indicated prior art problems of sulfonating petroleum with $SO_3$. The method can be operated to produce a high yield of petroleum sulfonate which is particularly rich in monosulfonated material.

In another aspect, the present invention provides liquid sulfonated petroleum compositions which not only are substantially homogeneous but which also have a high total sulfonated content and are produced extremely economically relative to mahogany sulfonate production costs. This sulfonate content is further characterized by having a high percentage of monosulfonates, which renders such compositions functionally equivalent or superior to mahogany sulfonates. The product compositions of the invention can be used in formulating micellar systems, without further treatment.

The invention is adapted for sulfonating a wide variety of petroleum oil feed stocks and is readily adapted for continuous, batch or quasi-continuous operation and may be carried out by adopting a large number of currently available processes and conventional apparatus.

The invention can be practiced so as to provide a method of sulfonating petroleum feed stocks wherein one can produce substantially any desired ratio of apparent monosulfonates to polysulfonates with relatively low amounts of undesirable salts.

Yet another novel feature of the invention is to mix a major amount of petroleum oil feed stock with a minor amount of an additive, such as, for example, a tallow alcohol or an oxo alcohol, feeding a liquid form of such mixture to a reaction zone, and introducing sulfur trioxide into the mixture to effect sulfonation. In a preferred embodiment, the mixture is in the form of a film and the sulfur trioxide is diluted with a stream of inert gas and this gaseous mixture is impinged into the liquid film.

Other and further features, aims, objects, purposes, advantages and the like will be apparent to those skilled in the art from the present disclosure.

DESCRIPTION

Sulfonation

During the course of the instant disclosure, it is to be understood and intended that the terms "sulfonation", "sulfonated" or equivalent, apply herein to any reaction which results in the substitution of a sulfo radical in a molecule of an initial starting material. Thus, it will be understood that these terms also encompass any sulfation reactions which may also be occurring, for example, with a petroleum oil feed stock containing a component having one or more hydroxy radicals per molecule. The hydroxy group of such component may or may not tend to react with sulfur trioxide. Thus, for example, such a component-type as naphthols or substituted naphthols, are apparently characteristically sulfonated through the ring radical rather than through the hydroxy radical in the practice of the method of this invention. Similarly, the petroleum oil feed stock components capable of reacting with a sulfonating agent, such as sulfur trioxide, are sometimes referred to as sulfonatable or sulfatable components, and, more generally, as sulfonatable or reactable components, and it will be understood that these terms all refer to petroleum oil components capable of reaction with a sulfonating agent.

PETROLEUM OIL STOCK

The petroleum oil feed stocks used as starting materials in the practice of this invention can be any petroleum oil feed stock known in the art. For example, gas oils, topped crude oils, heavy vacuum gas oils, lubricating oils, selected fractions recovered from lube oil treating processes, selected fractions from paraffinic, naphthenic, whole crudes, lightly distilled crudes, mixed base crudes or mixtures thereof. As workers in the art are well aware, extensive characterizations of petroleum oil stocks and/or crudes are available, for example, see "Evaluation of World's Important Crudes" (The Petroleum Publishing Co.), 1973, which contains a compilation of various characteristics of geographically diverse crude oils, while C. J. Thompson et al., "Hydrocarbon Processing—Analyzing Heavy Ends of Crude", September 1973, pages 123–130, characterizes the higher boiling fractions of five different crude oils of different chemical composition and geological origin. Similarly, the characteristic of various products obtained in refining petroleum or crude oil is known, for example, see W. L. Nelson, "Petroleum Refining Engineering", 4th Ed. (McGraw-Hill Book Co.). However, for purposes of the invention, such extensive characterizations are generally not required. Any available petroleum oil feed stock which contains sulfonatable components therein may be used in the practice of this invention. Thus, the petroleum oil feed stocks may be any natural material, or blend of natural and synthetic petroleum oils, including whole or partially refined natural crude oils, or portions thereof, such as synthetic oil stocks and mixtures of any of the above. The petroleum oil feed stocks may also contain waxes or may be partially or completely dewaxed petroleum oils. Another feed stock which may be employed as a starting material is a raffinate obtained in solvent refining of petroleum fractions. One may carry out such refining or extraction with various cyclic solvents, phenols, methyl ethyl ketones, liquid $SO_2$, etc. Both the resultant raffiante and the stripped extract may be subjected to sulfonation in accordance with the principles of the invention.

In many instances, petroleum oil feed stocks useful as starting materials in the invention exhibit a $-20°$ to $1400°$ F. ($-29°$ to $760°$ C.) (corrected atmospheric) boiling range (although higher and lower boiling feed stocks may also be used) and have an API gravity ranging between about $5°$ to $60°$ at $60°$ F. ($15.6°$ C.). Preferred petroleum oil feed stocks also include crudes which have aromatic portions with molecular weights in the general range of about 200 through about 1000 and more preferably in the range of about 250 through about 800, while the most preferred range is about 250 through 500. The amount of aromatic compounds or portions within a crude oil useful in the practice of this invention is generally about 10% to 95% (although purified synthetic feed stocks having 98% or more aromatic compounds therein are also useful in the practice of the invention), and more preferably about 20 to 80%, and most preferably about 25 to 75%, by weight of aromatics, as defined in the American Petroleum Institute Project 60 Reports 4–7 under "Characterization of Heavy Ends of Petroleum". Preferred petroleum oil feed stocks include Texas crude oil, Libyan crude oil, Louisiana Crude oil, California crude oil, Wyoming crude oil, Michigan crude oil, Illinois crude oil, Ohio crude oil, Oklahoma crude oil, Mississippi crude oil, Canadian crude oil, as well as various other geographically diverse crude oils. Preferred petroleum oil feed stocks also include crude oils having aromatic portions thereof which have a proton ratio of aliphatic radicals or compounds to aromatic radicals or compounds of approximately 3 through 20 and more preferably about 4 through 18. Lightly distilled or topped crude oils, for example, where at least a portion of the hydrocarbons boiling below about $680°$ F. ($320°$ C.) have been removed, may also be used as the feed stock. Of course, mixtures of various crude oils, or portions thereof, as well as blends may also be used as feed stocks in the practice of the invention.

The petroleum oil feed stocks may also be a material which is derived by subjecting a petroleum crude to one or more of the following general types of refinery processes, including thermal or catalytic processes: topping, reforming, cracking, alkylation, isomerization, polymerization, desulfurization, hydrogenation, dehydrogenation, distillation (including atmospheric and vacuum), sweetening, etc. Petroleum oils containing substantial amounts of aromatic compounds, naphthenic compounds and/or unsaturated compounds are also useful in the practice of the invention. Likewise, straight run or refinery naphtha streams may be sulfonated in accordance with the principles of the invention, although higher boiling fraction feed stocks are generally preferred. Also, petroleum oil stocks can be prepared by admixing together two or more different partially refined petroleum oils including crude oils so as to obtain, for example, some particular desired starting petroleum oil stock having a particular content of sulfonatable components and/or having a particular boiling range.

A wide variety of sulfonatable or reactable compounds or materials are characteristically present in various petroleum oil feed stocks, including aromatics, olefins, as well as alicyclic and aliphatic hydrocarbon compounds (and it is recognized that some alicyclic and aliphatic paraffins may be less reactable than some other compounds), etc., all of which various classes of materials are sulfonatable to variable degrees in accordance with the principles of the invention.

In order to estimate the amount of reactable or sulfonatable components in a selected petroleum oil feed stock, one may resort to a number of known procedures. For example, one may utilize an ASTM process, such as ASTM Test No. D848-62, which generally comprises feeding a petroleum oil feed stock with an excess of fuming (20%) oleum and then measuring the remaining layer of oil. A number of other methods, for example, a silica gel chromatography method, may be used in place of the exemplary method set forth above to determine a more or less approximate content of sulfonatable components in any petroleum oil feed stock (ASTM Test No. D2007).

In summary, a petroleum oil stock useful as a starting material in the practice of the present invention is characterized by:

(A) having an API gravity ranging from about 5° to 60° and somewhat more preferably from about 10° to 40° at 60° F. (15.6° C.);

(B) having a boiling point in the range of about $-20°$ to 1400° F. ($-29°$ to 760° C.) and somewhat more preferably from about 500° to 1100° F. (260° to 600° C.), corrected atmospheric; and (C) containing from about 10 to 95 weight percent (100 weight percent total stock basis) of sulfonatable components.

Preferred starting petroleum oil feed stocks may contain initially not more than about 3 to 10 weight percent (100 weight percent total stock basis) of combined elements selected from the group consisting of oxygen, sulfur and nitrogen and generally molecules containing such elements are not sulfonatable to any appreciable extent. Those skilled in the art will appreciate that petroleum oil feed stocks may also commonly contain quantities of water and of hydrocarbon molecules having incorporated thereinto atoms of oxygen, sulfur and nitrogen. In general, for purposes of the present invention, it is not necessary to eliminate such combined elements from a starting petroleum oil feed stock for use in the present invention, but it is preferred that a starting petroleum oil feed stock contain not more than the above indicated quantities of these elements.

ADDITIVES

In general, additives employed in this invention are organic species, characterized as organic radicals, a preponderance of which have attached thereto at least one proton replaceable by a sulfo group and at least one moiety selected from the group consisting of an aromatic nucleus, an olefinic carbon pair, and an oxygen atom directly bonded to a carbon atom by at least one bond. Typically and preferably, a given additive specie and/or molecule may have attached thereto a plurality of such protons and moieties and a plurality of different type additives may also be utilized. The presence of one or more of the additives in a liquid petroleum feed stock being subjected to a sulfonation reaction by this invention appears primarily to promote the compatibility of sulfonated oil components with unsulfonated or unsulfonatable oil components under reaction conditions, though there is no intent herein to be bound by theory or appearances. An apparent major function of an additive within the reaction system is to promote compatibility of reactants and reaction products under reaction conditions (and it is to be noted that these additives, after sulfonation, may have other functions in ultimate products of this invention). The additives seem to maintain an adequate solution or dispersion of petroleum oil components (reactants and reaction products) in such a way that adequate heat exchange and/or temperature control is effected between the sulfur trioxide or gas phase, the petroleum oil feed stock additive mixture or liquid phase and the heat exchange surfaces and/or reactor walls under the reaction conditions. Thus, the additives may be designated "compatibility promoting additives" and allow one to achieve an effective means of process and product control. The absence of one or more additive in an oil feed stock sulfonation process appears to result in gross component separation, lack of liquid compatibility, lack of uniform heat control, excessive polysulfonation, excessive sludge formation and an inability to maintain process control or reaction stability (although it is to be noted that certain low viscosity starting petroleum feed stocks and/or petroleum feed stocks mixed with solvents therefor, such as ethylene dichloride, trichloroethane, nitrobenzene, nitropentane, and the like may be at least partially sulfonated without the presence of a significant amount of additives). Nevertheless improved reaction products and reaction control apparently can be attained when at least some additives are present with the oil feed stock in the reaction zone. The additives also appear to reduce undesired oxidation of the oil feed stock, so that substantially less of, for example, reactant gaseous sulfur trioxide is lost via reduction to sulfur dioxide. For example, in prior art processes of sulfonating petroleum oil feed stocks with gaseous or liquid $SO_3$, as much as about 50% of the $SO_3$ is reduced to $SO_2$, depending on the degree of $SO_3$ input, oil type, etc. However, by following the principles of the invention, the loss of $SO_3$ is kept relatively low.

Also, the common prior art over-reaction of sulfonatable components in oil feed stock is apparently reduced by the presence of the additives so that less polysulfonates may be produced in the reaction products if so desired. In other words, the additives apparently provide an operator with a means for achieving some desired and substantially controlled ratio of monosulfonates to polysulfonates and equivalent weight distribution. For example, when a petroleum oil feed stock is divided into two portions for sulfonation, one of which is admixed with an additive and the other portion is sulfonated as such without an additive, and both such portions sulfonated under otherwise identical conditions and $SO_3$ treat levels, the products recovered in each instance have different equivalent weights and monosulfonate contents. The equivalent weight, ($\overline{EW}$), as determined by a silica gel analysis (ASTM Test No. D855-56) is almost invariably higher for the sulfonation product recovered from the portion containing the admixture of additive and oil feed stock. The monosulfonate content, as determined by a paratoluidine analysis is also generally higher for the product recovered from the portion containing the admixture of additive and oil feed stock. These results demonstrate that the addition of an additive to a petroleum oil feed stock undergoing sulfonation reduces the amounts of polysulfonates or low $\overline{EW}$ monosulfonate by-products (which are generally undesirable), as compared to prior art sulfonation of petroleum oil feed stocks without additions of additives. When an additive is present, the mono to disulfonate content in the active portion of the resultant product is generally in the 3:1 to 50:1 ratio whereas without an additive, the ratio of mono to disulfonate is at best about 1:1. At optimum $SO_3$ treat levels, sulfonation of an additive containing petroleum oil feed stock yields a product which is superior to a reaction product from a non-additive containing oil feed stock (i.e., a mahogany sulfonate). This superiority is shown by the higher $\overline{EW}$ and greater monosulfonate content in sulfonation products of an additive containing petroleum oil feed stock. At higher than optimum $SO_3$ treat levels, over-sulfonation occurs and a lower $\overline{EW}$ and lower monosulfonate content results. Accordingly, by a judicious selection of the amount of additive utilized and the $SO_3$ treat level utilized, an operator readily controls the amount of mono and polysulfonate in the ultimate sulfonation product.

The additives also tend to promote compatibility, solubilization, dispersion and/or coupling of the reaction products (sulfonated petroleum) with unreacted starting petroleum oil feed stock to yield a homogeneous or substantially homogeneous solution, dispersion and/or micellar solution, under sulfonation reaction conditions. While the exact chemical and/or physical functions of the additive described herein may not be fully understood, it is hypothesized that the additives somehow promote compatibility between unsulfonatable and/or unsulfonated components in admixture with an oil feed stock and the sulfonated components thereof. Observations taken during a film sulfonation reaction between unadulterated petroleum oil feed stocks and diluted gaseous sulfur trioxide lead to tentative conclusions that, as the sulfonatable components in the petroleum oil feed stocks become sulfonated, such sulfonated components tend to form an outer layer or boundary on the film or in a reaction mixture. At such outer location, the sulfonated components may be exposed to further sulfur trioxide and may tend to overreact, causing charring, polysulfonate formation, etc. Similar observations taken during a sulfonation reaction between a petroleum oil feed stock-additive mixture and diluted gaseous sulfur trioxide do not show any such outer layer, and it appears that the resulting sulfonated components remain within the film as a homogeneous mixture, a dispersion, or possibly an emulsion with the non-sulfonated components in the film, so that overreaction is substantially prevented or minimized, and the amount of polysulfonates in the ultimate product is characteristically materially reduced.

Of course, other explanations may be advanced as to the reason why the additives described herein promote increased yield of sulfonates during sulfonation of petroleum oil feed stocks and there is no intent to be bound herein by any theory or possible explanations.

As explained hereinabove, the additives also appear to enhance the attainment of a desired equivalent weight ($\overline{EW}$) range within the reaction product, which may be a mixture of various sulfonated and non-sulfonated compounds. The equivalent weight or $\overline{EW}$ of a sulfonate may be defined in the case of a salt as the combining weight thereof, i.e. the weight of sulfonate containing one gram atom of a cation (generally ammonium or sodium). For monosulfonates, the $\overline{EW}$ or combining weight is identical with the molecular weight. In the case of disulfonates, the combining weight is just one-half of the molecular weight but is nevertheless referred to as the equivalent weight thereof.

In other words, the $\overline{EW}$ of petroleum sulfonate or of the reaction products may be defined as the sulfonate molecular weight divided by the average number of sulfonate groups per molecule. The $\overline{EW}$ indicates the relative amount of monosulfonation and polysulfonation, i.e., the $\overline{EW}$ becomes lower as the polysulfonation increases.

The additives of the invention may be used as mixtures with suitable solvents or as mixtures among themselves. The additives themselves may undergo sulfonation or sulfation reactions and may result in a complex mixture with the other reaction products and may be usable as such or may be further processed before use thereof. Additives useful in the practice of this invention are chosen from a wide variety of chemicals, identified hereinafter, and which have the ability to effectuate at least one or more of the above discussed functions, such as promoting compatibility between sulfonated and unsulfonated and/or non-sulfonated oil feed stock components, decreasing and controlling viscosity during the sulfonation reaction, providing an adequate solution or dispersion of oil components (reactants and reaction products) in such a way that adequate or "stabilized" heat control and/or heat exchange is effected and thus providing a means of maintaining process control. Further functions of additives include: providing an improved sulfonation reaction; substantially increase the yield of petroleum sulfonates over the heretofore available processes; providing a control so that almost any desired ratio of monosulfonates to polysulfonates can be achieved with low amounts of undesirable salts; promoting the formation of adequate solutions/dispersions of reactants and reaction products under sulfonation and ultimate use (for example, in soluble, dispersion or micellar systems)conditions; providing a substantially theoretical yield of sulfonates from various oil feed stocks; providing improved operability in various continuous, batch, quasi-batch or quasi-continuous processes in various diverse apparatuses; reducing undesirable oxidation of the oil feed stock; provide a more efficient utilization of $SO_3$ so as to produce higher conversion to sulfonate activities as compared to reactions without additives; providing a mean of reducing or controlling viscosity of the sulfonation mixture; provide a means of effecting improved continuous sulfonation processes; reducing charring, oxidation and polysulfonation in the sulfonation reaction; reducing or preventing plugging or otherwise damaging reaction systems and components; being useful with an extremely wide variety of petroleum oil feed stocks; being adaptable to a wide variety of sulfonation processes and apparatuses; providing a means of achieving product composition control, i.e., by varying as desired the ratio of mono to polysulfonate and minimizing sludge formation; enhancing post-reactor digestion by reacting with any residual $SO_3$ or $H_2SO_4$ present in initial reaction products; providing an option to eliminating the need for extraction; providing a means for reacting $SO_3$ with oil feed stock at lower temperatures in comparison to reactions without additives; contributing to phase separation of acid from unreacted oil in the reaction products; capable of being hydrolyzed, if sulfated, so as to be removable from the reaction products if desired; providing a basis for solvent-free sulfonation; providing petroleum sulfonates which exhibit an enhanced oil recovery property; etc. Additive systems also apparently provide an important means of maximizing both high monosulfonation and commensurate sulfonate equivalent weight.

Generally, these additives comprise relatively high boiling organic compounds including unsaturated aliphatic hydrocarbons, substituted and unsubstituted aromatics, olefins, oxygen-containing compounds, esters (especially high boiling esters), ethers, ether esters (especially high boiling ether esters), certain catalytic phase oils, polymer distillation residues, mixtures of alkylated benzenes and naphthalenes, mixtures thereof, alkoxylated derivatives of such compounds, and the like. These additives generally comprise organic compounds generally containing from 2 through 30 carbon atoms within their main hydrocarbon chain and may contain more carbon atoms, for example, in side chains or in alkoxylated additives condensed onto the main compound or radical. Such organic compounds are of a type which promote compatibility of unsulfonated (sulfonatable and non-sulfonatable) petroleum oil feed stocks with sulfonated components during $SO_3$ reaction conditions. Compounds of this type generally have boiling points in the range from about 212° to 932° F. (about 100° to 500° C.) or higher, depending upon the degree of substitution, if any. Additionally, such compounds generally are comprised of unsulfonatable organic radicals having an average atomic weight in the range of from about 55 through 6000, and somewhat more preferably in the range from about 75 through 1000, and most preferably in the range of from about 100 to 350 (excluding any alkoxy or the like units, which may range up to about 1000 or more, attached thereto) and a preponderance of such organic radicals each have attached thereto at least one proton replaceable by a sulfo group and at least one moiety selected from the group consisting of an aromatic nucleus, an olefinic carbon pair, and an oxygen atom directly bonded to a carbon atom by at least one bond.

Preferred groups of organic additives useful in the practice of the invention are selected from the classes consisting of alcohols, oxygen-containing compounds, hydroxy-containing compounds, substituted and unsubstituted hydrocarbons, high boiling esters, high boiling ethers, high boiling ester ethers, aromatic compounds, fatty acids and derivatives thereof, olefins, ketones, alkaryl compounds and mixtures thereof. A preferred class among this group is the oxygen or hydroxy-containing compounds, both of which are sometimes referred to hereinafter as "oxygenated" or oxygen-containing compounds.

A species of the oxygenated compounds (which include the hydroxy-containing compounds) useful in the practice of the invention comprise aliphatic alcohols. Typical aliphatic alcohols useful in the practice of the invention are those which contain at least 4 carbon atoms per molecule (although $C_1$ to $C_3$ aliphatic alcohols may be used when such low molecular weight alcohols are alkoxylated with a plurality of alkoxy units) and preferably are $C_6$ to $C_{28}$ aliphatic alcohols. Mixtures of aliphatic alcohols (some of which may be alkoxylated) may also be used in the practice of the invention. For example, one may employ octyl alcohol, nonyl alcohol, decyl alcohol, hexyl alcohol, octadecyl alcohol, dodecyl alcohol, lauryl alcohol, myristyl alcohol, palmityl alcohol, stearyl alcohol, etc. or mixtures thereof. A particularly useful aliphatic alcohol is a tallow alcohol (which is a mixture of $C_{14}$ to $C_{18}$ fatty alcohols).

Another useful species of oxygen-containing or oxygenated compounds comprises phenolic compounds which include substituted phenolic compounds. Typical phenolic compounds comprise phenol, octyl phenol, nonyl phenol, resorcinol, etc. as well as phenol compounds having one or more $C_1$ to $C_{16}$ alkyl thereon, $C_2$ to $C_4$ alkoxylated phenols (including alkoxylated alkyl phenols), polyalkoxylated (including polyalkoxylated polyalkyl phenols) phenol including mixed polyalkoxylated phenols, i.e., ethylene oxide-propylene oxide units, or mixtures thereof.

A further useful species of oxygen or hydroxy-containing compounds comprises glycol and glycerol compounds, such as propylene glycol, butylene glycol, ethylene glycol, diethyl glycerol, etc. all of which may be alkoxylated, if desired.

Yet a further useful species of oxygen or hydroxy-containing compounds comprises organic acids, such as $C_4$ to $C_{22}$ fatty acid, which may also be alkoxylated, if desired.

A preferred species of oxygenated (hydroxy-containing) compounds useful in the practice of the invention are commercially available high-boiling alcohol-containing materials known as oxo alcohols or oxo bottoms and more particularly as oxo alcohol still bottoms, oxo alcohol distillation residue, oxopolymer products or oxo alcohol polymer bottoms. The preparation and description of these alcohol materials is known, for example, as set forth in a book entitled "Higher Oxo Alcohols" by L. F. Hatch, Enjay Company, Inc., 1957, the disclosure of which is incorporated herein by reference. The term "oxo alcohol" is used in the art as descriptive of the type of process employed in producing these alcohols synthetically. Alcohols having the desired functionality can also be obtained from natural sources as well as from available synthetic processing means, and functionality is not dependent on the source or synthesis process. Generally, oxo alcohols comprise a complex mixture of various alcohols, ether alcohols, esters, soaps, etc., for example, as described by E. H. Bartlett et al. in an article entitled "Oxo Ether Alcohols", published in Industrial and Engineering Chemistry, Vol. 51, No. 3, March 1952, the disclosure of which is incorporated herein by reference. Commercially available oxo alcohols include those in the $C_4$ to $C_{18}$ range and two particularly attractive oxo alcohols are the $C_8$ and $C_{10}$ materials, both of which are mixtures of isomers produced by the oxo process from branched $C_7$ and $C_9$ olefins. A typical oxo alcohol still bottom of this type which is useful in the practice of the invention has the following composition:

| Component | % By Weight |
|---|---|
| Octyl alcohol | 2-20 |
| Nonyl alcohol | 5-40 |
| Decyl and higher boiling materials* | 25-90 |
| Esters | 20-80 |

*Ether alcohols, saturated and unsaturated ethers, mixtures thereof, as well as other oxo reaction by-products.

Another oxo alcohol still bottom which is an excellent additive useful in the practice of the invention has the following composition:

| Component | % By Weight |
|---|---|
| Octyl alcohol | 5 |
| Nonyl alcohol | 10 |
| Decyl and higher boiling materials* | 35 |
| Esters | 45 |
| Soaps | 5 |

*Ether alcohols, saturated and unsaturated ethers, mixtures thereof, as well as other oxo reaction by-products.

Any of the above oxygen or hydroxy-containing compounds may also be alkoxylated by a reaction with a select number of mols, say about 1 to 200 mols, of a $C_2$–$C_4$ alkoxide, i.e., ethylene oxide, propylene oxide, butylene oxide, an ethylene oxide-propylene oxide unit or mixtures thereof.

Another class of additives useful in the practice of the invention comprise high boiling unsaturated (olefins) branched or straight-chain hydrocarbons (i.e. having a boiling point in the range of about 100° to about 500° C.). Generally, these compounds comprise $C_4$ to $C_{28}$ hydrocarbons and preferably are $C_8$ to $C_{22}$ hydrocarbons, such as, for example, $C_{14}$ or $C_{18}$ α-olefins, mesityl oxides, tetradecene, octocosene, docosene, octodecene, etc., or mixtures thereof.

Yet another useful class of additives useful in the practice of the invention is high boiling ethers, i.e., having a boiling point in the range of about 100° to about 500° C. Typical members of this class are glycol ethers, such as available under the trademark "CELLOSOLVE" from Union Carbide Corporation, and which include such ethers as 4-methoxy butanol, 2-ethoxy ethanol, 2-propoxy ethanol, 2-butoxy ethanol, etc. Other typical ethers useful herein are those available under the trademark "CARBITOL" from Union Carbide Corporation and which include such ethers as diethylene glycol ethyl ether, diethylene glycol butyl ether, etc. The preferred glycol ethers include $C_4$ to $C_6$ glycol ethers, such as diethylene glycol, etc.

Another class of additives useful in the practice of the invention is high boiling ether esters (i.e., having a boiling point in the range of about 100° to 500° C.), such as available under the trademarks "CARBITOL" or "CELLOSOLVE". Typical materials of this type are "CARBITOL" acetates such as methoxy diethylene glycol acetate or "CELLOSOLVE" acetates such as methoxy ethyl acetate, butoxy ethyl acetate, etc.

Yet another class of additives useful in attaining an improved degree of reaction between petroleum oil feed stocks and gaseous sulfur trioxide is the alkaryl compounds, typically comprising $C_7$ to $C_{30}$ compounds having a boiling point in the range of about 100° to 500° C. Typical materials of this type include $C_1$ to $C_{20}$ alkyl substituted benzenes, such as dodecylbenzene, cumene, thymol (p-propyl-m-cresol), etc.

An additional class of additives useful in the practice of the invention is esters. Typically, preferred esters having boiling points in the range of from about 100° to 500° C. and comprise $C_1$ to $C_4$ alkyl esters of $C_4$ to $C_{22}$ aliphatic carboxylic acids, for example, methyl, ethyl, etc., esters of octyl, nonyl, decyl, lauryl, myristyl, palmityl, stearyl, etc. acids or mixtures thereof. A preferred group of such alkyl ester acids are the methyl esters of $C_8$ to $C_{18}$ fatty acids, and, of these, the methyl esters of $C_8$ to $C_{10}$ and $C_{10}$ to $C_{18}$ are extremely useful. Useful esters may also be produced by reacting the above $C_6$ to $C_{20}$ aliphatic acids with the $C_6$ to $C_{28}$ aliphatic alcohols described earlier, all of which may be alkoxylated, if desired.

Further additives useful in the practice of the invention include catalytic cycle oil, such as defined in U.S. Pat. No. 3,317,422 (column 1, lines 55-72), which is incorporated herein by reference, ultraformer polymer bottoms (a known commercially available material principally comprised of mixtures of alkylated benzenes and naphthalenes, and mixtures thereof), as well as other like materials.

In summary, an additive useful as a starting material in the practice of the present invention is characterized by:

(A) being comprised of unsulfonatable organic radicals possessing an average molecular weight from about 55 to 6000;

(B) having a boiling point in the range from about 100° to 500° C. (212° to 932° F.) corrected atmospheric pressure, and (C) a preponderance of such radicals each having attached thereto at least one proton replaceable by a sulfo group and at least one moiety selected from the group consisting of an aromatic nucleus, an olefinic carbon pair, and an oxygen atom directly bonded to a carbon atom by at least one bond. (Of course, polyfunctional molecules having a plurality of such protons and moieties attached thereto are also included as are various blends of additives.)

Additives useful in the present inventon can initially be admixed with other organic materials, such as alkane hydrocarbons, halogenated hydrocarbons, and the like, which do not appear to undergo sulfonation when exposed to sulfur trioxide. Preferably at the time of use in the practice of this invention, however, an additive composition contains a preponderance (i.e., not less than about 60 weight percent, total additive composition basis) of at least one additive characterized as above.

PROCESS DETAILS

In proceeding along the principles of the invention and in accordance with one of the more preferred embodiments of the invention, the petroleum oil feed stock is first mixed with an additive. In general, mixtures employed in the present invention comprise from about 0.5 to 15 weight percent of an additive, and from about 85 to 99.5 weight percent of a petroleum oil stock, on a 100 weight percent total mixture basis. Preferably, a mixture employed in the present invention comprises from about 2 to 10 weight percent of an additive and from about 98 to 90 weight percent of a petroleum oil stock on a 100 weight percent total mixture basis.

Preferably, in one mode, a film of such mixture is fed to a reaction zone of a reactor, such as a tubular reactor. A selected additive may be added if desired from a source thereof to an already formed film of oil feed stock prior to or simultaneously with $SO_3$ contacting or such may be mixed with an oil feed stock prior to being fed, in film form, to a reaction zone. The mixture or just the petroleum oil feed stock may be heated prior to $SO_3$ contact, if desired.

The reaction zone generally is one compatible with the reaction of gaseous $SO_3$ (sulfur trioxide) and a sulfonatable material. A wide variety of existing processes and apparatuses incorporate and utilize suitable reaction zones. Examples of such prior art processes and apparatus include U.S. Pat. Nos. 2,697,031; 2,768,199; 2,923,728; 3,056,831; 3,270,038; 3,328,460; 3,427,342; 3,438,742; 3,438,743; and 3,438,744.

The contacting of sulfur trioxide with a mixture of petroleum oil stock and additive as above characterized is affected generally at a temperature ranging from about 25° to 200° C. (about 77° to 392° F.) although if solvents, such as liquid $SO_2$, are utilized, lower temperatures may be used. In the reaction from about 5 to 40 parts by weight of sulfur trioxide are contacted typically with each 100 parts by weight of the (essentially moisture-free) mixture comprised of petroleum oil stock and additive being sulfonated. The total time of contacting of sulfur trioxide with such mixture is at least sufficient to sulfonate not less than about 10 weight percent of the total sulfonatable components present in the starting petroleum oil stock.

Preferably, such contacting is continued for a time at least sufficient to produce a sulfonated composition which comprises a composition of this invention, as hereinafter defined.

Since temperature, time and pressure conditions are not critical and may be readily adjusted by an operator in accordance with a particular apparatus, process or desired end product, all such conditions will sometimes be referred to herein as "time-temperature-pressure conditions" sufficient to form sulfonation products One excellent and commercially feasible method for continuous sulfonation is set forth by Knaggs et al. in U.S. Pat. No. 3,169,142 (owned by the instant assignee), the disclosure of which is incorporated herein by reference. The method thereof, which will be described in further detail hereinafter is improved by the instant invention, particularly in relation to sulfonation of petroleum oil feed stocks. However, it will be appreciated that the invention may also be practiced by various other sulfonation methods, such as batch, cascading, quasi-continuous, etc.

Generally, the contacting time varies from about 0.001 seconds or less to about 1800 seconds or more, depending on the type of apparatus used, the desired degree of sulfonation, the extent of recycling (if any) of the reactants and/or reaction products, etc.

As set forth earlier, a mixture of starting petroleum oil feed stocks and additive is fed, in a liquid form, which, in the preferred embodiment under discussion, comprises flowing a film of such mixture to a reaction zone of a reactor. In such a preferred embodiment, the liquid film of petroleum feed stock and additive is supported on a supporting and confining heat exchange surface defining the reaction zone. An apparatus which includes such a surface may comprise a tubular or multiple tube reactor, such as described in the above referenced Knaggs et al. U.S. Pat. No. 3,169,142. Of course, in other processes, such as for example, in a batch $SO_3$ sulfonation process, the liquid mixture is simply fed to a reaction vessel which may include either a heat exchange surface along select portions thereof, or a cyclic looped external heat exchanger.

The sulfonation reaction of this invention can be carried out using a gaseous $SO_3$, optionally admixed with an inert gas, such as nitrogen or air. Generally, the ratio of inert gas to gaseous $SO_3$ falls within the range of from about 3:1 to 75:1 and preferably from about 5:1 to 50:1. In certain instances, it may be desirable to utilize liquid $SO_3$, admixed with or without a liquid or gas diluting agent, such as for example, $SO_2$ refined light paraffinics, light crude oil distillates, air, nitrogen, pentane, and the like, and such a liquid mixture is within the scope of the invention. An effluent diluent-gas can be recycled and $SO_3$ added thereto to thereby provide a closed system. Further, if desired, $SO_3$ may be utilized per se whether in liquid or gaseous form, although from a point of safety and reaction control, it is preferable to utilize a mixture of gaseous $SO_3$ and an inert gas. The gas mixture is preferably caused to impine on the liquid petroleum-additive mixture and readily reacts with the sulfonatable components of such liquid as soon as sulfur trioxide comes in contact with at least some of the reactable components present in the liquid. This reaction is exothermic and good heat exchange capabilities may be required in the reaction system, such as by providing a reaction surface having a heat exchange means associated therewith or by providing an operable external heat exchange system.

The amount of additive present in the reaction zone generally is at least about 0.5% by weight based on the weight of starting petroleum feed stock. Generally, the amount of compatibility promoting additive utilized in accordance with the principles of the invention range from about 0.5% to about 15% by weight and a practical additive dosage is about 0.5% to 5% or 2% to 10% (same basis). As those skilled in the art will appreciate, the exact or optimum amount of additive utilized with a selected petroleum oil feed stock is dependent upon a wide variety of variables, such as characteristics of the oil feed stock, desired degree of sulfonation, availability of a select additive, etc., and a specific amount for use in a given system may be readily determined by those skilled in the art.

The selection of particular reaction conditions, such as time, temperature, pressure, etc., depend upon a number of process variables, such as characteristics of petroleum oil feed stock, the amount and type of additive, the apparatus employed, the characteristics of the formed product, etc. Generally, the sulfonation is conducted using temperatures in the range of about 25° to 200° C. (77° to 392° F.) and somewhat more preferably in the range of about 50° to 140° C. (122° to 284° F.). It is recognized that measurements of true reaction temperature under the dynamic conditions present within a reactor are very difficult to measure accurately. However, such temperatures can be estimated, for example, by means of thermocouple in the reaction zone and by observing the resultant temperature profile. The sulfonation process may also be run above or below atmospheric pressures.

As noted above, the invention is adaptable to be used with a wide variety of prior art processes and apparatuses, upon which the invention is a substantial improvement. Thus, a particular reaction vessel may be in a horizontal, vertical or angularly inclined position, and be adapted for continuous, batch, quasi-continuous or cascading operation. Preferably, the reactable mixture is in the form of a falling liquid film, since such falling films appear to have advantages of improved reaction control, better versatility, simplicity of design and large-scale continuous operation as well as other advantages.

A preferred basic sulfonation process is described in the above Knaggs et al. U.S. Pat. No. 3,169,142. Briefly, sulfonation is carried out in accordance with that process by inducing marked turbulence in a liquid film containing sulfonatable components with a pressurized stream of an inert diluent and vaporized sulfur trioxide which is impinged onto such a film. The inert diluent is gaseous and may be dry air, "SO₃ converter gas" from a sulfur burner catalytic converter which generally comprises a mixture of 5 to 10% $SO_3$ in dry air, nitrogen, carbon dioxide, carbon monoxide, sulfur dioxide, methane, ethane, propane, butane, pentane mixtures thereof or other dry gases. The diluent gas may be passed only once or it may be recycled in the process, as desired.

As the Knaggs et al. process is practiced in accordance with the principles of the instant invention, a selected petroleum oil feed stock mixed with an additive is caused to flow along the inner walls of a single tube or preferably a plurality of downwardly inclined reactor tubes in a film form. The film of the oil-additive mixture (which may be preheated) is impinged upon by a dilute vaporized sulfur trioxide reagent at substantial velocities so as to create marked turbulence in the film. The sulfonation reaction itself is extremely fast, with the residence time of the sulfur trioxide inert gas mixture, which is usually directed into contact with the film by means of a suitable gas inlet device, characteristically being less than about 0.5 seconds. The gas temperature in an exemplary embodiment ranges from about 25° to 80° C. (about 77° to 179° F.) at a line pressure ranging from about 2 to 20 psi. The reactor itself may be of a single tube or a plurality of tubes of various diameters and lengths. To effect such a desired rapid reaction and rapid heat exchange, marked turbulence should be produced in the reaction zone, and the Knaggs et al process provides sufficiently rapid reaction times and heat exchange capabilities.

By proceeding in accordance with the principles of the invention, the extent or degree of reaction between oil feed stocks and sulfur trioxide is increased on the order of 200% when additives are added to the petroleum oil feed stock prior to sulfonation reactions, as compared to similar reactions where no additive has been added. Under certain conditions, the increase in the extent of reaction is as high as 500% in comparison with prior art sulfonation processes involving no additives.

Products

In general, a product of this invention is a mixture of petroleum oil feed stock and additive, as explained above, which has been sulfonated with sulfur trioxide, as explained above. Such a product comprises a substantially homogeneous liquid under reaction conditions and typically is sulfonated to an extent such that at least about 10 weight percent of the sulfonatable components thereof are sulfonated (total product composition weight basis).

One preferred product of this invention may be regarded as a substantially homogeneous (preferably liquid) sulfonated petroleum composition which comprises on a 100 dry organic weight percent total weight basis:

(A) from about 5 to 98 weight percent of monosulfonated hydrocarbon;

(B) from about 0 to 50 weight percent of polysulfonated hydrocarbon; and (C) from about 2 to 90 weight percent of non-sulfonated petroleum.

Such a product composition is prepared by contacting a liquid hydrocarbon mixture with a gaseous sulfur trioxide composition at a suitable temperature, all as described above.

Many of the described additives are also sulfonated or sulfated wholly or partially during the sulfonation reaction between petroleum oil feed stocks and sulfur trioxide. For example, the alcohol additives and the ether alcohol additives are generally sulfated during such reaction, while the alkaryl additives may be sulfonated during the reaction. Such fully or partially sulfonated additive derivatives also function as additives as such, and may be initially added to a petroleum oil feed stock to promote compatibility between petroleum sulfonates and oil under the reaction conditions or may be blended with the ultimately attained reaction products as an aid in forming stable micellar dispersions used in oil recovery processes. Further, these additive derivatives do not detract from the useful characteristics of the ultimate reaction product and may remain therein. In some instances, high additive levels may be preferred to further enhance oil recovery properties, particularly in higher salinity systems, etc. In certain instances, it may be desirable to separately sulfonate select additives and admix such separately sulfonated additives with sulfonated petroleum products (which may or may not include additives therein).

The ultimate reaction products of the invention with or without further treatment, such as neutralization, may be used without further purification (such as phase separation, etc.) and generally comprise a mixture of petroleum sulfonates, unsulfonated petroleum feed stock components, sulfonated and unsulfonated additives, along with various other minor constituents, such as salts. If desired, the sulfonates may be separated and/or the additives recovered for recycling, however, from an economical viewpoint, such further purification or separation of materials may not be justified. Further, if neutralized, the amount of alkali (such as NaOH, NH₄OH KOH, etc.) may be so controlled that the resultant products have a pH in the range of about 3 to 12 and preferably in the range of 6–10.

The reaction products and/or components thereof, such as the petroleum sulfonates have numerous fields of use, for example, as industrial surfactants, as blending agents for lubricating oils, as surface-active agents, as emulsifiers, dispersants, etc. A particularly attractive use for the reaction products of the instant sulfonation process (with or without the presence of additives, which themselves may be sulfonated) is in petroleum recovery operations, particularly as surfactants for aiding the recovery of crude oils from so-called depleted fields or wells, for example, as described by G. P. Ahearn in an article in the Journal of American Oil Chemists' Society, October 1969 (Vol. 46), pages 540A et seq., entitled "Surfactants for Oil Recovery" or in U.S. Pat. No. 3,302,713, both of which are incorporated herein by reference. The petroleum sulfonate products obtained in the practice of the invention are extremely useful in forming so-called dispersion or micellar systems and/or emulsions as well as other systems which are used in enhanced or secondary recovery of petroleum. The petroleum sulfonates obtained in the practice of the invention may be added to or used to replace all or part of various other surface-active agents in various prior art oil recovery systems, such as described, for example, in U.S. Pat. Nos. 3,254,714; 3,297,084; 3,307,628; 3,330,343; 3,348,611; 3,356,138; 3,368,621; 3,476,184; 3,493,047; 3,493,048; 3,497,006; 3,500,912; 3,504,744; 3,506,070; 3,506,071; 3,653,440; 3,769,209; 3,830,301; 3,873,453; 3,885,626; and 3,885,628 (all of which are incorporated herein by reference), as well as in other somewhat similar systems. In many instances, no further changes in the compositions of such oil recovery systems, whether micellar, dispersion, emulsion or otherwise, will be required. In other instances where larger or smaller amounts of petroleum sulfonates (reaction products) obtained in the practice of the invention are required, workers skilled in the art can readily determine the optimum amount by routine production of a desired system and routine evaluation of such system, for example, with the aid of core-flooding tests or the like.

FURTHER PROCESSING OF PRODUCTS

In further embodiments of the invention, the above described basic petroleum oil sulfonation process may be supplemented by a number of further optional processes. For example, the reaction products (a mixture of petroleum sulfonates, unsulfonated oils, sulfonated and unsulfonated additives, etc.) may be subjected to neutralization, extraction, deoiling and/or desalting processes. Generally, proper selection of the type and amount of additive and control of the reaction conditions in the basic sulfonation process minimizes an excessive presence of unsulfonated oils and/or salts in the reaction products (typicaly the amount of salts in neutralized products may range from about 0.1 to 10% by weight); and in many instances these further processing steps may be avoided. This constitutes a further advantage of the invention. However, in those instances where such optional steps are desired, they may be performed, for example, by adding water or a mixture of water and an alcohol, such as $C_1$–$C_5$ alcohols or semipolar organic compounds, for example, isopropyl alcohol or benzene to the reaction products to achieve a phase separation and then simply removing the unsulfonated (unsulfonatable and non-sulfonated) oils or raffinate phase, which is substantially insoluble in the hydrophilic solvent. If desired, the unsulfonated oils may be recycled through the sulfonation reaction or may be otherwise disposed of and any alcohol or other valuable component therein recovered for further use. This deoiling process may be followed by a desalting process whereby the acidic reaction products are neutralized to form a desired salt, such as with sodium or ammonium hydroxide and the resultant salt precipitates from the alcoholic solution, which can then be separated by centrifugation filtration, etc. (although small amounts of salt may remain in the product without detrimental effect). The deoiling process may also be performed on the neutralized reaction products, if so desired, and since some solvent may carry over with the extracted phase, such phase may be distilled or otherwise purified to recover any solvent therein for further use, or left in, if desired. Separation, such as may occur on cooling of essentially unreacted oils from crude sulfonic acid mixtures may be effected by decantation or other phase separating processes.

Additionally, the reaction products may be subjected to a digestion process whereby the reaction products are held or stored in a container for some period of time, such as 20 minutes, while they are maintained at some desired temperature or cooled down from the heat of reaction. In a modified form of the digestion process, the reaction products are maintained at a select temperature and some heat may be applied. Such a digestion process is recommended to react traces of dissolved sulfur trioxide with sulfonatable oil components and/or sulfonatable additive components and to reduce the sulfuric acid content in the reaction products.

The digestion process may be coupled with a number of further steps. For example, additional amounts of additives may be intermixed with the reaction products during digestion or thereafter. Many of the additives described herein tend to further reduce the sulfuric acid content and react with any sulfur trioxide present in the reaction products. The additives added at this stage may be the same or different from those present in the sulfonation reaction zone.

A further optional treatment of the sulfonation reaction products comprises a sequential combination of digestion and heat treatment. Typically, after digestion, the reaction products are heated or held at a temperature ranging from about 35° to about 150° C. (95° to 302° F.) for a brief period of time. This combination of steps is designed to further complete the sulfonation reaction and reduce the sulfuric acid content in the ultimate reaction products.

Yet a further optional treatment of the reaction products involves digestion, followed by heat treatment and further addition of additives to effect a complete reaction as set forth above.

In addition, other conventional steps may be utilized following the initial sulfonation reaction, such as degassing, filtration and/or neutralization. For example, the sulfonation reaction products, which are acidic in nature, may be first neutralized, such as with an economical material, for example, sodium hydroxide, followed by removal of resultant salt, as by the addition of a suitable solvent and then followed by filtration, centrifugation, etc.

Thus, one has the option of utilizing any combination of the post-sulfonation steps described hereinabove to achieve desired characteristics in the reaction product. Under certain reaction conditions, generally at somewhat higher reaction temperatures, immediate neutralization of the reaction products is preferable so as to avoid decomposition of reaction products, possible desulfonation or other undesirable reactions.

EMBODIMENTS

With the foregoing general disclosure in mind, a number of detailed examples are presented which will illustrate to those skilled in the art the manner in which this invention is carried out. However, the examples are not to be construed as limiting the scope of the invention in any way and the examples merely point out the efficacy of the invention in attaining the high degree or extent of reaction between sulfonatable components of various oil petroleum feed stocks with gaseous sulfur trioxide in the presence of the additives described hereinabove and demonstrate a preferred utility of the so-attained sulfonated compositions.

EXAMPLE 1

In the first series of experiments, a high boiling heavy oil fraction was subjected to sulfonation, utilizing the techniques of Knaggs et al U.S. Pat. No. 3,169,142. The petroleum feed stock oil is characterized as a heavy vacuum gas oil derived from Wyoming crude oil. Other characteristics of this oil feed stock as well as other oil feed stocks are shown in Table A below and this oil is proportioned into individual run proportions, each of which is sulfonated in a six-foot tube by subjecting a liquid film containing the allotted oil sample (with and without select additives) to impingement by a mixture of nitrogen and sulfur trioxide, at a ratio of 95 to 5 of nitrogen to sulfur trioxide reagent. The nitrogen-sulfur trioxide gas temperature at initiation of the reaction was about 35° C. (95° F.). The pressure of the gas during the reaction zone was 4–5 psig. The various oil allottments being sulfonated were heated to a feed temperature of about 50°–55° C. (122°–131° F.). The reactor tube was steam-jacketed and the product outlet temperature was around 110° C. (230° F.).

Without benefit of an additive, the total active or sulfonate content that could be obtained with the above feed stock was about 10%. When attempts were made to drive the reaction to completion by gradually approaching a 1:1 mol ratio of $SO_3$ to petroleum oil (sulfonatable component content), the reaction products began to deposit on the walls of the reactor tube and charring was noted, the pressure fluctuated, and eventually the tube became plugged to the extent that the reaction had to be shut down.

In further runs under the above reaction conditions, various additives (enumerated in Table I below) were first added to run allotted amounts of the above otherwise unadulterated oil feed stock and a mixture of additive and oil feed stock was then heated to the above feed temperature and subjected to sulfonation reaction as set forth above.

The following Table outlines results obtained with various additives (the characterization of which are summarized in Table B below). The oil feed stock itself contained about 56.5% sulfonatable (aromatic) compounds, and thus the maximum theoretical sulfonate content in the final product that could be achieved was about this amount. In many instances, nearly theoretical sulfonate yields were obtained. In each case, in the presence of the selected additive, good flow was noted and no process difficulties were encountered.

In the examples that follow, unless otherwise stated, the terms "oxo", "oxo alcohol" and "oxo bottoms" refer to a technical or crude grade (unrefined) of distillation bottoms or residue resulting from the distillation of the reaction products derived from the so-called oxo alcohol synthesis process. Higher forms of purity, higher cost versions, and blended oxo bottoms are also quite usable in the process.

TABLE I

| | (A) SULFONATION REACTION PRODUCT | | | | | | | |
|---|---|---|---|---|---|---|---|---|
| | Acidity (me/g) | | | % | % | % | % | |
| Additive++++ | Total | P—Toluidine+ | Aniline++ | MS* | PS** | TS*** | UM**** | $H_2SO_4$ |
| 3% Oxo bottoms | 2.02 | 0.87 | -- | 37.0 | 16.5 | 53.5 | -- | -- |
| 5% Ethoxylated tallow alcohol | 1.89 | 0.91 | 0.42 | 39.2 | -- | -- | -- | 2.1 |
| 5% Ethoxylated phenol | -- | -- | -- | -- | -- | -- | -- | -- |
| 2% Ethoxylated phenol | -- | -- | -- | -- | -- | -- | -- | -- |
| 5% Oxo bottoms | -- | -- | -- | -- | -- | -- | -- | -- |
| 5% Diethylene glycol monoethyl ether | 1.96 | 0.62 | -- | 26.5 | -- | -- | -- | -- |
| 5% Ethoxylated nonyl phenol | 2.51 | 0.70 | -- | -- | -- | -- | -- | -- |
| 5% Ethoxylated nonyl phenol | 2.31 | 0.66 | 0.44 | 28.5 | -- | -- | 57.3 | 2.16 |
| 5% Ethoxylated nonyl phenol | 2.32 | 0.76 | 0.74 | 32.6 | -- | -- | 52.0 | 3.6 |
| 3% Diethylene glycol monoethyl ether | 2.62 | 0.74 | 0.26 | 31.8 | -- | -- | 52.1 | 1.3 |
| 3% Diethylene glycol monoethyl ether | 2.35 | 0.74 | 0.76 | 31.8 | 27.7 | 59.5 | 52.7 | 3.8 |
| 3% Oxo bottoms | 2.57 | 0.83 | 0.92 | -- | -- | -- | -- | 4.6 |

| | (B) Ammonium Salt Product | | | | | |
|---|---|---|---|---|---|---|
| Additive++++ | % MS* | % PS** | % TS*** | % UM**** | $H_2O$ | Average Equiv. Wt.§ |
| 3% Oxo bottoms | -- | -- | -- | -- | -- | — |
| 5% Ethoxylated tallow alcohol | 2.82 | -- | -- | -- | -- | — |
| 5% Ethoxylated phenol | -- | -- | -- | -- | -- | — |
| 2% Ethoxylated phenol | 26.1 | -- | -- | -- | -- | — |
| 5% Oxo bottoms | 30.0 | -- | -- | -- | 5.8 | — |
| 5% Diethylene glycol monoethyl ether | 25.2 | -- | -- | -- | 4.0 | — |
| 5% Ethoxylated nonyl phenol | 30.0 | -- | -- | -- | -- | — |
| 5% Ethoxylated nonyl phenol | -- | -- | -- | -- | -- | 395 |
| 5% Ethoxylated nonyl phenol | 30.1 | 4.8 | 34.9 | 56.0 | 5.5 | 423 |
| 3% Diethylene glycol monoethyl ether | -- | -- | -- | -- | -- | — |
| 3% Diethylene glycol monoethyl ether | -- | -- | -- | -- | -- | 400 |

TABLE I-continued

| | | | | | | |
|---|---|---|---|---|---|---|
| 3% Oxo bottoms | 33.5 | 8.7 | 42.2 | 51.9 | 1.3 | 411 |

MS* Estimated Monosulfonate
PS** Estimated Polysulfonate [100% − (UM H$_2$O + Salt + MS) = PS]
TS*** Estimated Total Sulfonate [MS + PS]
UM**** Estimated Unmodified Oil (by a standard petroleum ether extraction)
+Analysis for Monosulfonate Content as determined by a p-toluidine method assuming only monosulfonates respond and assuming a given molecular weight (350 + 80)
++Analysis for Sulfuric Acid Content
-- Flow of reactants through tube good; process under control; no reactor plugging and no detailed analysis was made.
§Calculated sulfonate ≡ω [MS + PS], and spot verified by silica gel analysis
+++Additional characteristics of the additives are present in Table B
— Not determined

EXAMPLE II

An extract of a petroleum oil feed stock identified as SAE 20 heavy lubricating oil stock (which had been subjected to a phenol extraction process) was utilized as the oil feed stock. This feed stock had the following characteristics:

therein. Attempts to increase the extent of reaction resulted in poor material flow through the reaction zone and back pressure fluctuations in the diluted gaseous sulfur trioxide and was followed by charring (localized overreaction) and subsequent tube plugging.

The results attained by use of various additives are set forth in Table II below, and it can be seen that excellent sulfonation results were obtained:

TABLE II

| | (A) SULFONATION REACTION PRODUCT | | | | | | | |
|---|---|---|---|---|---|---|---|---|
| | Acidity (me/g) | | | % | % | % | % | |
| Additive+++ | Total | P—Toluidine+ | Aniline++ | MS* | PS** | TS*** | UM**** | H$_2$SO$_4$ |
| 5% Oxo bottoms | 1.27 | 0.59 | 0.075 | 26.7 | 16.5 | 43.2 | 68.4 | 0.37 |
| 3% 2-butoxy ethanol | 2.11 | 0.82 | 0.62 | 37.2 | -- | -- | 55.0 | 3.1 |
| 3% Acetate ester of diethylene glycol monoethyl ester | 1.67 | 0.67 | 0.25 | 30.2 | 20.0 | 50.2 | 60.0 | 1.2 |
| 5% C$_{8-10}$ Alcohol | 2.37 | 0.81 | -- | 36.8 | -- | -- | -- | -- |
| 3% C$_{8-10}$ Alcohol + 2% C$_{8-10}$ Fatty methyl ester | 1.98 | 0.76 | 0.77 | 34.3 | -- | -- | 59.9 | 3.75 |

| | (B) Ammonium Salt Product | | | | | |
|---|---|---|---|---|---|---|
| Additive+++ | % MS* | % PS** | % TS*** | % UM**** | H$_2$O | Average Equiv. Wt.§ |
| 5% Oxo bottoms | 30.2 | 3.2 | 33.4 | 68.4 | -- | 430 |
| 3% 2-butoxy ethanol | 25.1 | 11.3 | 34.4 | 55.0 | -- | 412 |
| 3% Acetate ester of diethylene glycol monoethyl ester | -- | -- | -- | -- | -- | — |
| 5% C$_{8-10}$ Alcohol | 28.8 | -- | -- | 48.6 | -- | — |
| 3% C$_{8-10}$ Alcohol + 2% C$_{8-10}$ Fatty methyl ester | 24.0 | -- | -- | -- | -- | 459 |

MS* Estimated Monosulfonate
PS** Estimated Polysulfonate [100% − (UM H$_2$O + Salt + MS) = PS]
TS*** Estimated Total Sulfonate [MS + PS]
UM**** Estimated Unmodified Oil (by a standard petroleum ether extraction)
+Analysis for Monosulfonate Content as determined by a p-toluidine method assuming only monosulfonates respond and assuming a given molecular weight (350 + 80)
++Analysis for Sulfuric Acid Content
-- Flow of reactants through tube good; process under control; no reactor plugging and no detailed analysis was made.
§Calculated sulfonate ≡ω [MS + PS], and spot verified by silica gel analysis
++++Additional characteristics of the additives are present in Table B
—Not determined

| | |
|---|---|
| Molecular weight | 373 |
| API Gravity | 12.7 |
| Color | Dark |
| Viscosity | 210° F. = 91 SSU |
| Sulfur | 1.5-2% |
| Pour Point | +70° F. |
| Viscosity Index | −53 |
| Aromatics | 75% | and was subjected to a number of sulfonation reactions in a manner outlined in Example I, without an additive and with the various additives enumerated in Table II below. Without additions of an additive, the sulfonation reaction could only be made to yield a sulfonation product having about a 10% sulfonate content, whereas the oil feed stock was reported to have about 75% aromatics (presumably mostly sulfonatable) components

EXAMPLE III

A petroleum oil feed stock identified as AMOCO Oil LF5991 and generally characterized as a heavy gas oil was subjected to a phenol extraction refining process, and the extract had a molecular weight of about 330 to 340 and a sulfonatable content (as aromatics) of about 75% (and it will be appreciated that some aromatics may be unsulfonatable because of steric hindrance or the like). This extract was subjected to a series of sulfonation reactions in accordance with Example I, without an additive and with various additives. In this series of experiments, the reaction products were analyzed only for the total amount of petroleum sulfonates and unmodified (unsulfonated) oil. The results are set forth below in Table III:

TABLE III

| Additive++++ | Ammonium Salt Product | | | |
|---|---|---|---|---|
| | % TS*** | % UM**** | Average Equiv. Wt.§ | Reaction Conditions and Observations |
| 9% $C_8$–$C_{10}$ fatty acid methyl ester | 44.7% | 57.3% | 432 | Reaction maintained at 100° C.; good flow; slight sludge; no plugging. |
| 9% Isopropyl palmitate | 65.2% | 39.2% | 432 | Reaction at 100° C.; fair flow; slight pressure fluctuation; slight sludge buildup; no plugging. |
| 9% Hydrogenated $C_{12}$–$C_{16}$ fatty acid methyl esters | 64.9% | 36.2% | 432 | Reaction at 100° C.; fair flow; slight pressure fluctuation; slight sludge buildup; no plugging. |
| 9% Butoxy ethyl acetate | 23.5% | 83.0% | 432 | Reaction at 100° C.; good film flow; slight sludge buildup; no plugging. |
| 9% $C_8$–$C_{10}$ fatty acid | 68.3% | 37.0% | 432 | Reaction at 100° C.; very good flow; no pressure fluctuation; no plugging. |
| 9% Branched chain $C_{15}$ alkyl benzene | 55.0% | 47.1% | 432 | Reaction at 100° C.; poor film flow; pressure fluctuation; slight plugging. |
| 9% Stoddard Solvent[1] (a petroleum distillate having a flash point of 100–110° F.) | 38.0% | 68.0% | 432 | Reaction at 100° C.; poor film flow; pressure fluctuation; slight plugging. |
| 9% Perchloroethylene[1] | 47.6% | 59.2% | 432 | Reaction at 100° C.; poor film flow; pressure fluctuation; slight plugging. |
| 9% Branched chain crude dodecylbenzene | 51.2% | 42.8% | 432 | Reaction at 100° C.; poor film flow; pressure fluctuation; slight plugging. |
| 9% Palmitic acid | 66.7% | 44.0% | 432 | Reaction at 100° C.; good film flow; slight pressure fluctuation; no plugging. |
| 9% $C_{14}$ α-olefin | 53.5% | 52.0% | 432 | Reaction at 100° C.; excellent film flow; no pressure fluctuation; very slight sludge formation. |
| 9% $C_{18}$ α-olefin | 54.1% | 45.5% | 432 | Reaction at 100° C.; good film flow; very slight pressure fluctuation; very slight sludge formation. |
| None | 49.0% | 52.2% | 432 | Reaction at 100° C.; considerable pressure fluctuation; discontinuous film flow; plugging. |
| 9% Mesityl oxide | 20.0% | 83.5% | 432 | Reaction at 100° C.; good film flow; undersulfonated. |
| 9% The acetate ester of ethylene glycol monoethyl ether | 56.1% | 41.2% | 432 | Reaction at 100° C.; very good film flow; no pressure fluctuation; very slight sludge formation. |
| 9% Mesityl oxide | 43.8% | 52.0% | 432 | Reaction at 100° C.; very good film flow; very little sludge formation. |
| 9% Trichlorobenzene[1] | 43.5% | 60.0% | 432 | Reaction at 100° C.; slight pressure fluctuation; slight sludge formation; no plugging. |

TS*** Estimated Total Sulfonate [MS + PS]
UM**** Estimated Unmodified Oil (by a standard petroleum ether extraction)
++++Additional characteristics of the additives are present in Table B
§Calculated sulfonate ≃ω [MS + PS], and spot verified by silica gel analysis
[1]This additive was functional, even though it did not yield optimum results.

EXAMPLE IV

A petroleum oil feed stock identified as AMOCO Oil LF5978 whole crude which contained about 48% aromatics was subjected to a series of sulfonation reactions in accordance with Example I, with and without an additive. The results are set forth below:

TABLE IV

| Additive++++ | % TS*** | % UM**** | Average Equiv. Wt.§ | Reaction Conditions and Observations |
|---|---|---|---|---|
| 9%[2] $C_{14}$ α-olefin | 25.2% | 71.8% | 432 | Reaction at 100° C.; good material flow; slight sludge formation. |
| None | 14.6% | 85.0% | 432 | Reaction at 100° C.; pressure fluctuation; sludge formation; plugging. |

TS*** Estimated Total Sulfonate [MS + PS]
UM**** Estimated Unmodified Oil (by a standard petroleum ether extraction)
++++Additional characteristics of the additives are present in Table B
§Calculated sulfonate ≃ω [MS + PS], and spot verified by silica gel analysis
[2]No attempt was made to optimize sulfonate yield.

EXAMPLE V

A high molecular weight crude oil feed stock, which had the following analysis:

| | |
|---|---|
| Molecular Weight | 435 |
| Distillation Range | 824°–989° F. (corrected) |
| Sulfur, wt. % | 1.55 |
| Aromatics, wt. % | 64.9 |

-continued

| | |
|---|---|
| Saturates, wt. % | 35.1 |
| Gravity °API | 17.2 |
| Viscosity, SSU at 100° F. | 2271 |
| Viscosity, SSU at 210° F. | 89.0 |
| Appearance | Soft Grease (at 70° F.) | was mixed with 2% to 4% of an oxo alcohol (identified as Houdry $C_8$ alcohol bottoms), heated to about 100° C. and then subjected to continuous $SO_3$ sulfonation under the following conditions:

| | |
|---|---|
| Feed rate | 6 lbs./hour |
| Feed temperature | 90°–110° C. |
| Air flow | 5 - 5 SCFM |
| $SO_3$ flow | Approx. 0.5 lbs./hour |

-continued

| Reactor jacket | Steam |
|---|---| and the reaction products were collected into an NH₄OH solution.

Under visual observation, a continuous film formed on the reactor walls and maintained a uniform appearance throughout the reaction. At the end of the reaction, the reactor drained relatively clean and analysis of actives indicated that very small amounts of polysulfonates were formed. The results are set forth below in Table V:

TABLE V

| | Analysis on Solids Basis | | |
|---|---|---|---|
| Additive++++ | Actives+++ | T UM**** | Average Equiv. Wt.§ |
| 2% Oxo Alcohol | 40.0 | 57.1 | 532 |
| 3% Oxo Alcohol | 51.5 | 42.9 | 532 |
| 4% Oxo Alcohol | 50.1 | 45.8 | 532 |

+++Actives - estimated Monosulfonate
UM**** Estimated Unmodified Oil (by a standard petroleum ether extraction)
++++Additional characteristics of the additives are present in Table B
§Calculated sulfonate c̄ω̄ [MS + PS], and spot verified by silica gel analysis

EXAMPLE VI

A petroleum oil feed stock identified as AMOCO LF-7050 and generally characterized as a vacuum gas oil, which had the following analysis:

| Molecular Weight | 386 |
|---|---|
| Sulfur, % wt. | 2.64 |
| Gravity °API | 21.9 |
| Viscosity, SSU at 100° F. | 254 |
| Viscosity, SSU at 210° F. | 46.9 |
| Aromatics, % wt. | 47.2 |
| Naphthenes, % wt. | 37.3 |
| Paraffins, % wt. | 15.5 |
| Distillation Range | 600°-1100° F. | was mixed with 0% to 3% oxo alcohol and subjected to a sulfonation reaction under conditions similar to those set forth in Example V. At 0% oxo alcohol, the film visually appeared as a discontinuous "cottage cheese" like material and the buildup of sludge on the walls of the reactor was of such magnitude that within a relatively short period of time the reactor became plugged and the reaction had to be shut down. As the concentration of additive increased, the sludge buildup decreased to a point where, after completion of the reaction, the reactor drained substantially clean. The results are set forth below in Table VI:

TABLE VI

| | Analysis on Solids Basis | | | | |
|---|---|---|---|---|---|
| Additive++++ | % Actives+++ | % UM**** | % PS** | % Salt | Average Equiv. Wt.§ |
| None | — | — | — | — | — |
| 2% Oxo Alcohol | 45.0 | 54.4 | -- | -- | 483 |
| 3% Oxo Alcohol | 45.0 | 55.8 | -- | -- | 483 |

TABLE VI-continued

| | Analysis on Solids Basis | | | | |
|---|---|---|---|---|---|
| Additive++++ | % Actives+++ | % UM**** | % PS** | % Salt | Average Equiv. Wt.§ |
| Alcohol | 40.5 | 35.7 | 20.8 | 3.0 | 483 |

+++Actives - estimated Monosulfonate
PS** Estimated Polysulfonate [100% − (UM H₂O + Salt + MS) = PS]
UM**** Estimated Unmodified Oil (by a standard petroleum ether extraction)
++++Additional characteristics of the additives are present in Table B
§Calculated sulfonate c̄ω̄ [MS + PS], and spot verified by silica gel analysis
-- Not determined

EXAMPLE VII

A petroleum oil feed stock identified as Marathon feed stock TL8-15-69 characterized as having an average molecular weight of about 409 was mixed with 1.5% oxo alcohol and subjected to sulfonation conditions similar to that set forth in Example V. The reaction progressed satisfactorily with no buildup of pressure in the gas line and no plugging of the reactor. No analysis was made of the reaction product, although it is assumed an analysis thereof would be similar to that of earlier reaction products.

EXAMPLE VIII

A petroleum oil feed stock identified as Cross 9 Stock Hydro-F oil and generally characterized as a lube oil feed stock which had the following analysis:

| Gravity, °API at 60° F. | 20.0 |
|---|---|
| Viscosity, SSU at 100° F. | 950 |
| Viscosity, SSU at 210° F. | 70 |
| Aromatics, % wt. | 47.7 |
| Saturates, % wt. | 48.8 |
| Distillation Range | 980°-1090° | was mixed with 3% oxo alcohol and subjected to sulfonation conditions similar to that set forth in Example V. The reaction progressed satisfactorily and no gas line pressure fluctuation was observed. The reaction products were collected in NH₄OH and analyzed on solids basis. A first sample showed 31.2% monosulfonate actives and 70.8% unmodified oil. A second sample, which was purposely over-sulfonated to determine total sulfonatables present in the feed stock, showed 31.1% monosulfonate actives (by paratoluidine) and 62.8% unmodified oil (thereby indicating about a 8% increase in polysulfonate content).

EXAMPLE IX

A petroleum oil feed stock identified as Clark FCC clarified oil, which had the following analysis:

| Molecular Weight | 283 |
|---|---|
| Gravity, °API at 60° F. | 5.7 |
| Distillation Range | 484°-947° F. (corrected) | was mixed with 3% oxo alcohol and subjected to sulfonation conditions similar to that set forth earlier. Good flow characteristics were observed with no gas pressure fluctuation. The reaction products were collected in NH₄OH and upon analysis showed a 63.6% unmodified oil.

EXAMPLE X

A petroleum oil feed stock identified as a Shell "DU-TREX" 315 (a registered trademark) oil, which had the following analysis:

| | |
|---|---|
| Gravity °API | 17.4 |
| Viscosity, SSU at 100° F. | 307 |
| Viscosity, SSU at 210° F. | 45.0 |
| Distillation Range | 645°–742° (corrected) |
| Aromatics, % wt. | 60.2 |
| Saturates, % wt. | 33.0 |
| Average mol. wt. | 285 | was divided into two portions, one portion was sulfonated as is under reaction conditions similar to that set forth earlier and the other portion was mixed with 5% oxo alcohol and then sulfonated under similar reaction conditions. The unadulterated oil showed an uneven flow and a cottage cheese-like appearance in the film, with plugging of the reactor. The additive modified oil showed good flow characteristics and no process problems were encountered. The reaction products were collected and upon analysis showed 43.1% actives and 56.9% unmodified oil.

In each of the foregoing Examples I through X, the sulfonates were derived using the preferred embodiment, namely, via continuous $SO_3$ falling film sulfonation and employing the sulfonation additive incorporated into the petroleum feed stock.

EXAMPLE XI (A) The petroleum oil feed stock of Example IV, identified as AMOCO OIL LF5978 whole crude, was sulfonated by a batch process. A jacketed reaction vessel of suitable size was provided with 465 grams of the oil feed stock and 23 grams of oxo alcohol. A sparger was inserted into the reaction mixture and air bubbled through the sparger to keep the liquid reactants out of the interior thereof. The reactants were heated to about 90° C. and a holding flask for liquid $SO_3$ was heated. When the $SO_3$ began to vaporize, air flow to the sparger was cut off and gaseous $SO_3$ (without any inert or diluent gas therein) was fed through the sparger and into contact with the heated reactants. The sulfonation reaction proceeded smoothly with no pressure fluctuation or sparger plugging occurring. After the reaction was completed and the reaction product removed from the reactor, only minor amounts of "sludge" remained on the walls thereof. Following neutralization of the product with a 50% NaOH a product analysis was conducted and the results were as follows:

| | |
|---|---|
| Actives | 14.3% (pTH, Assumed MW 506) |
| U.M. | 55.8% |
| Water | 7.6% |
| Salt | 6.0% (assumed) |
| Polysulfonate | 16.3% (difference) |
| Average Eq. Wt. | 506 |

(B) The above batch sulfonation process was repeated with different oil feed stocks, identified as Transmission Pipe Line (Mid-Continent) and with the above identified whole crude oil and substantially the same results were obtained.

The foregoing demonstrates that the principles of the invention may be readily adapted to batch operation where desired. For example, in certain oil recovery operations it may be economically practical to produce a select size batch of petroleum sulfonate at the field so that transportation and the like costs for shipping feed stocks and/or reaction products may be dispensed with.

EXAMPLE XII (a) The above batch experiment (Example XI) was substantially repeated with the oil feed stocks of Example XI but the additive was omitted from the reaction vessel. After about half of the $SO_3$ had been added (in vaporized form and without an inert gas), gas line pressure fluctuations were noticed, indicating that sludge was building up on the sparger and momentarily closing the outlets thereof. The thermometer (which was inserted within the reactants to monitor the temperature of the reaction) and the sparger began to vibrate as if insoluble materials were being thrown against these objects so that the experiment was halted.

After dismantling the apparatus, it was found that both the sparger and thermometer had a thick viscous sludge buildup around the parts thereof which had been immersed in the reactant. Also, the inner walls of the reaction flask had a considerable amount of sludge adhering to it.

(B) The above batch experiments were further repeated with the AMOCO OIL LF5978, as used in Examples IV and XI feed stock but 6% oxo alcohol bottoms was introduced into the reaction flask prior to the introduction of $SO_3$. The feed stock-oxo mixture was heated to 90° C. and then the $SO_3$ was vaporized and slowly added to this mixture. After about 40 minutes, all of the $SO_3$ had been added with no pressure fluctuation or vibration being observed. After the product was removed from the reactor, only trace amounts of sludge were detected on the reactor walls. After neutralization of the product with concentrated $NH_4OH$, the product was analyzed as 12.0% actives (pTH, MW 506) and 5%.

(C) The above experiment was repeated with the Mid-Continent oil feed stock (Example XI, Run B) and 4% oxo additives was provided within the reaction vessel prior to the start of the sulfonation reaction and air was used as an inert diluent for the $SO_3$ (95:5-air:-$SO_3$). No pressure fluctuations were observed during the reaction and very little sludge precipitated on the reactor walls. After neutralization of the product with $NH_4OH$, the product was analyzed as 18.5% actives ($\overline{EW}$ 506) 5.3% water and 19.5% actives/solids. This product was then allowed to settle overnight and the top oil layer was then decanted, leaving a residue which contained 32% actives.

From the above experiments, it is apparent that the presence of the additives of the invention provide for an improved batch operation.

EXAMPLE XIII

A "continuous batch recycle" or quasi-continuous apparatus was set up for sulfonating an oil feed stock identified as topped Mid-Continent Transmission Pipeline Crude Oil or Marathon Topped Crude Oil PPL2538 (approximately 23% of initial distillation forerun removed). The apparatus utilized comprised a fresh oil feed stock tank connected by a suitable line and pump means for adding oil as desired to an enclosed reaction vessel, which was fitted with a mechanical stirrer; a $SO_3$ supply tank connected by suitable lines and pumps to a vaporizer and then for discharge into the upper portion of the reaction vessel; a discharge line connected between the bottom of the reaction vessel to a heat exchanger and from there back to the upper portion of the reaction vessel. Appropriate valves were placed in the various lines for control of material flow and small amounts of reaction product were withdrawn from the discharge line prior to the heat exchanger. The various pumps and valves were adjusted to provide the following flow rates: oil feed stock at 196 grams/min.; $SO_3$ flow rate at 19.6 grams/min.; recycle rate at 2–3 gals./min. and product removal rate at 216.2 grams/min. and two runs were performed in this apparatus.

Run 1. The first run was conducted without any additives and 6000 grams of the above identified oil feed stock was charged into the reaction vessel and the recycle pump was activated, along with heat exchanger so as to heat the circulating oil to about 70° C. The $SO_3$ vaporizer was then activated and gaseous $SO_3$ was fed into the reaction vessel so that the sulfonation reaction was initiated. These conditions were maintained for about 30 minutes at which time it was calculated that about a 10% "treat" level ("treat" level refers to parts of $SO_3$ added to 100 parts of oil feed) had been achieved in the reactor. At this time, the fresh oil pump was activated so that new feed stock was pumped into the reactor vessel and the product removal pump was activated to remove a portion of the recycling material. Samples were taken approximately every 20 or so minutes. The reaction was terminated after about 3 hours. Total product recovered on shutdown and from the samples was about 34,491 grams. The total amount of $SO_3$ added was about 3254 grams, the total amount of oil feed stock utilized, including the initial charge, was about 32,460 grams so that the total weight of reactant was about 35,694 grams.

The reactor was kept warm and allowed to drain for about 2 hours. When the reactor was opened, a relatively thin coating of solid material was noted on all interior surfaces and several large chunks of solid material were found. The recycle line was then disassembled for inspection and a relatively thick coating of viscous material was noted in this line, especially on the horizontal portions thereof. The heat exchanger was removed and allowed to drain overnight in a vertical position. It was then weighed at 3125 grams and subjected to a thorough cleaning and re-weighed so that the material left in the heat exchanger after drainage could be calculated. This amount was found to be 15 grams; thereafter the remaining apparatus was cleaned and prepared for the next run.

6400 grams of the reaction product obtained from the first run was then charged into a 3-neck 12 liter flask fitted with a stirrer and 525 grams of 50% NaOH was slowly added with stirring. The maximum temperature attained during this neutralization was about 70° C. and the pH of the mixtures was 8.2. Preliminary analysis indicated that 8.4% acid product (as $SO_3$) was present in this reaction product.

Run 2. A second run was then conducted in the above "continuous batch recycle" apparatus as described above under substantially identical conditions and with identical oil feed stock but 4% oxo bottoms was intermixed with the feed stock prior to reaction.

5760 grams of the oil feed stock and 240 grams of commercially available $C_8$ oxo alcohol bottoms (Houdry Process & Chemical Co., Del.) was charged into the reactor vessel and recycled via the heat exchanger until a temperature of about 68° to 72° C. was attained. Then the $SO_3$ vaporizer was activated and gaseous $SO_3$ was brought into contact with the oil-additive mixture. Thereafter, the procedure of the first run was followed and the reaction allowed to proceed for about 3 hours with periodic product samples being taken during that time. After the reaction was terminated, the reactor was allowed to drain and the total amount of product collected amounted to about 33,484 grams.

The reactor was then opened for inspection and one relatively large chunk of solid material and some much smaller ones were found. The interior walls of the reactor had a substantially thinner coating of material than was noted in the first run. The recycle line was disassembled for inspection and it was noted that this line was much cleaner than after the first run. The heat exchanger was re-weighed after draining overnight in a vertical position and after thorough cleaning so that the amount of product left in the heat exchanger after drainage could be determined. This amount was found to be only 2.5 grams as compared with 15 grams found in the heat exchanger in the first run (without additive).

244 grams of the reaction product obtained from the second run was then charged into a 3-neck 2-liter flask fitted with a stirrer and 22 grams of 50% NaOH was slowly added with stirring. The temperature of the neutralization reaction was about 70° to 60° C. and the pH of the neutralized mixture was about 8.0. Preliminary analysis indicated that 10% acid product (as $SO_3$) was present in the reaction product.

In order to better compare the results of runs 1 and 2, the following Table summarizes the pertinent data therefrom:

TABLE XIII

|  | Run 1 | Run 2 |
|---|---|---|
| Oil feed stock | Topped crude | Topped crude |
| Additive | None | 4% oxo bottoms |
| Batch phase | 0.5 hr. | 0.5 hr. |
| Continuous phase | 3.0 hrs. | 3.0 hrs. |
| Est. recycle ratio | 20:1 | 20:1 |
| Reactor pressure (PSIG) | 10–28 | 10–15 |
| Reactor temperature | 70° C. | 70–73° C. |
| Heat exchanger temp. | About 65° C. | About 65° C. |
| Calc'd. $SO_3$ "treat" level | 8.4% | 10% |
| Appearance of reactor/equipment surfaces | All surfaces coated with a heavy deposit | Much less deposition |
| Weight of residue in heat exchanger after 24 hrs. drainage | 15 grams | 2.5 grams |
| Neutralized product | Na salt | Na salt |
| Total sulfo actives (silica gel) | 16.8% | 19.69% |
| Oil (silica gel) | 69.32% | 71.6% |
| $Na_2SO_4$ | 7.0% | 4.95% |
| $H_2O$ (K.F.) | 6.6% | 7.9% |
| Sulfonate eq. wt. | 501 | 574 |
| p. toluidine (est. mono. suf.) | 0.155 me/g | 0.226 me/g. |
| Assumed monosulfonate content | 7.8% | 13.0% |
| Estimated mono/total sulfonate | 46.3% | 65.9% |

As can be deducted from the foregoing runs, substantial operational process advantages are attained by incorporating additives, such as the oxo alcohol entity used hereinabove (which was sometimes interchangeably referred to as oxo alcohol distillation residue, oxo alcohol bottoms, oxo alcohol polymer or polymer material, etc., and it will be appreciated that all of which terms refer to the same entity), in quasi-continuous cyclic batch process and provide similar advantages therein as in batch and continuous systems, i.e., substantially less "gumming up" of reactor surfaces, pipes, etc. In addition, the foregoing experiment shows that incorporation of an additive, such as oxo alcohol into a topped crude oil or some other petroleum oil feed stock provides the following advantages: yields high apparent monosulfonate (basis of p-toluidine HCl analysis); yields high average sulfonate equivalent weight; yields lower amounts of derived $Na_2SO_4$, which indicates less oxidation; etc.; provides a higher conversion of $SO_3$ to actives; requires less operating pressure, which tends to indicate a lower $SO_2$ generation; yields higher sulfoactives; lowers "gumming" residue deposit on reactor surfaces (2.5 grams versus 15 grams); etc.

Petroleum sulfonates derived from the process disclosed in the instant invention are useful in recovery of in-place oil, for example, after primary oil production methods have been terminated. After a subsequent waterflood is terminated, an oil reservoir often retains 40%–60% of the total petroleum originally in place. The petroleum may be retained by adsorption on the formation surfaces, or it may be retained due to capillary forces which are larger than the forces driving the fluids through the reservoir. Because of the greater abundance of water-wet reservoirs, the latter retention mechanism is most often considered to be dominant. (See J. J. Taber, Soc. Pet. Eng. J. 9 (1969) 3–12). The capillary pressures may be overcome by increasing the producing pressure in the reservoir or by reducing the interfacial tension between the aqueous phase and the oil. Because increasing the pressure in the reservoir to a sufficient degree is technically very difficult (if not impossible), the only known workable technique is to reduce the interfacial tension.

Studies indicate that the interfacial tension must be lowered to approximately less than $10^{-3}$ dynes/cm to effectively produce oil. An aqueous solution of petroleum sulfonates at low concentrations (0.001 to 30%) may often produce these low interfacial tensions. In addition, microemulsions (stable, translucent, micellar solutions of oil, water, electrolytes, a surfactant and often another amphiphilic compound such as an alcohol) are often used, which are miscible with both the oil and water contained in the reservoir. These solutions, in effect, reduce the interfacial tensions to zero because of the mutual miscibility. Petroleum sulfonates are often used as the surfactant because of their low cost and ability to produce stable microemulsions. These solutions are often placed in a reservoir and in turn displaced by thickened water or mobility control agents to maintain favorable mobility ratios and prevent the drive fluid from passing the microemulsion.

EXAMPLE XIV

An oil recovery sulfonate was prepared by $SO_3$ sulfonation essentially as disclosed in Examples I-X by sulfonating a mixture of 95% petroleum oil, characterized as having an API gravity of 13.0 at 60° F.; a viscosity at 210° F. of 58.3; an aniline point of 96.5° F., a weight % of phenol of 0.084; a weight % of aromatics of 75.3; a weight % of asphaltenes of 0.0; a weight % of polar compounds of 8.0; and a weight % of saturates of 16.7 plus 5% oxo alcohol bottoms. An oil recovery system was formulated as follows: 3.75 parts crude sulfonate (39.3% active sulfonate having an $\overline{EW}$ 453); 0.75 parts hexyl alcohol; 1.5 parts sodium chloride; 200 ppm calcium ions; 200 ppm magnesium ions, diluted with up to 100 parts Houston, Tex. tap water. Standard test cores were first flooded or saturated with distilled water containing 1.5% NaCl and 200 ppm of Mg++ and Ca++, respectively; then these cores were flooded to irreducible water saturation with a Robinson, Ill. crude oil stock and were then flooded to about 32% residual oil with the above water solution. Thereafter, the cores were flooded with the above oil recovery material at a rate of 1 foot per day of displacement. The calculated displacement of oil achieved was 62.5%.

This demonstrates that the sulfonation products of the invention (which include mixtures of oil sulfonates and additives, whether sulfonated or not; oil sulfonates per se; and mixtures thereof) are useful in enhanced oil recovery process. Of course, the reaction products (surfactants) of the invention may also be utilized in other oil recovery systems, whether water external or otherwise.

A preferred use of the reactor products of the invention is in the production of soluble or dispersible systems for oil recovery as set forth above. Systems utilized in oil recovery generally comprise a mixture of a hydrocarbon, an aqueous material and petroleum sulfonates. In certain instances, other surfactants and/or electrolytes may also be added. In typical micellar systems, which are presently of substantial interest to the art, the amount of hydrocarbon present may vary from about 2% through 90%; the amount of aqueous material may vary from about 5% through 95%; the amount of active petroleum sulfonate is generally about 1 to 25%; the amount of a synergistic surface-active agent may vary from about 0.01% through 10% and the amount of an electrolyte may vary from about 0.001% through 5%. The sulfonation products of the invention may also be used in other soluble or dispersible systems, including water-soluble and/or oil-soluble systems in varying amounts as desired. Typically, an oil field, generally during or after secondary recovery, is injected with an amount equal to about 1 to 50% pore volume of the field of the surfactant system comprised of water and/or oil and containing about 0.001 to 30% by weight of a sulfonation reaction product of the invention along with lesser amounts of compatible electrolyte and other synergistic surfactants and thereafter a mobility control agent is injected.

The hydrocarbon used in such dispersions or soluble systems may be a crude oil, a partially refined fraction of a crude oil or a refined fraction of natural crude oil or a synthetic hydrocarbon, for example, a halogenated hydrocarbon, the aqueous material may be soft water, water containing minor amounts of salt or the like, or even brackish water. The other surfactant may be an amine aldehyde, a ketone, a hydroxy-containing compound, such as a conventional alcohol, ester, ether, etc., having a $C_1$ to $C_{20}$ chain therein. The electrolyte may be an organic salt or base or even an organic acid. Further details and compositions of such systems are available in the art, for example, cited earlier herein.

EXAMPLE XV

A petroleum oil feed stock containing 4.0% oxo alcohol bottoms was sulfonated in the continuous falling film sulfonation process following essentially the same procedure as disclosed in Examples I through X. The petroleum oil was characterized as follows:
Average mol. wt=390
Gravity ° API 14.0 (at 60° F.)
Specific gravity 0.972
Distillation range—696° to 918° F.
Aromatic content—70%.
The resultant acid was collected and maintained at 70° C. for thirty minutes during which time two layers formed. The upper oil layer was removed. The bottom crude acid layer was neutralized with sodium hydroxide and was found to be 41.0% active with an $\overline{EW}$ of 437 (by silica gel analysis), a sample of acid produced under similar conditions but not oil-decanted was found to be 33.4% actives (p-toluidine).

EXAMPLE XVI

A petroleum oil feed stock (characterized in Example XV) containing 4% oxo alcohol bottoms was sulfonated continuously following essentially the same procedure as disclosed in Examples I–X. The crude acid recovered from this sulfonation was neutralized with sodium hydroxide, yielding a petroleum sulfonate with 39.1% actives (silica gel) which was analyzed as containing a 445 equivalent weight of sulfonate. To 500 grams of this crude sulfonate was added 500 milliliters of tap water and 500 milliliters of 95% isopropyl alcohol and these components were mixed together and allowed to stand for thirty minutes during which time three distinct layers formed. The smaller upper layer was removed and found to contain mostly unreacted oils. The middle layer was removed and the isopropyl alcohol therein was removed by distillation, the resultant petroleum sulfonate so derived had the following analysis:

65% actives (having an average equivalent weight of sulfonate of about 438)
9.0% oil
18.9% water
6.7% sodium sulfate.

The lower layer was also small in size and contained essentially inorganic salts and water. Thus, this procedure can be utilized to provide a substantially higher actives and lower free oil-bearing sulfonate.

EXAMPLE XVII

Unrefined petroleum sulfonate described in Examples XV and XVI (prior to any deoiling step) was formulated into the following oil recovery systems:

FORMULA A

| | | |
|---|---|---|
| 27.81% | 2.75 pts. | Crude sulfonate (at 31% actives having an $\overline{\epsilon\omega}$ of 445) |
| 27.81% | 2.75 pts. | Chicago tap water |
| 35.38% | 3.40 pts. | Crude oil (Benton, Illinois field) |
| 6.47% | 0.64 pts. | Ammonium salt of sulfonated C$_8$ oxo alcohol bottom (at 50% actives) |

FORMULA A-continued

| | | |
|---|---|---|
| 2.53% | 0.25 pts. | Hexanol |
| 100% | 9.89 pts. | Total |

FORMULA B

| | | |
|---|---|---|
| 26.07% | 2.75 pts. | Crude sulfonate (at 40% actives having an $\overline{\epsilon\omega}$ of 445) |
| 26.07% | 2.75 pts. | Chicago tap water |
| 33.18% | 3.50 pts. | Crude oil (Benton, Illinois field) |
| 11.37% | 1.20 pts. | Ammonium salt of sulfonated C$_8$ oxo alcohol bottoms (at 50% actives) |
| 2.37% | 0.25 pts. | Hexanol |
| .95% | .0 pts. | Sodium chloride |
| 100% | 10.55 pts. | |

Formula A was unstable when 0.10 pts. of NaCl added, whereas Formula B was stable.

This example demonstrates in this instance th higher level of sulfonated oxo alcohol bottoms as in Formula B provides greater salt tolerance tha Formula A and hence provides a more flexible useful oil recovery system.

The crude sulfonate in the above formulations derived from a mixture of about 4% oxo alcohol toms and about 96% petroleum feed stock. Analy: the crude sulfonate indicates that the mixture conta approximately 3% oxo sulfate and 37% petroleum fonate.

EXAMPLE XVIII

A number of the reaction products of the inve: were formulated into oil recovery slugs and ce commercially available mahogany sulfonates wer tained and formulated into similar oil recovery s These slug formulations were then tested with star cores of sandstone to determine their respectiv recovery efficiency.

In order to better emphasize and highlight any d ences between the petroleum sulfonates utilized in tests, extremely low slug pore volumes (concentr of surfactant in total pore volume of test core) utilized and it will be appreciated that higher slug volumes may typically, although not necessaril utilized.

TABLE XVIII

| Petroleum Sulfonate Analysis | | | | |
|---|---|---|---|---|
| | WITCO 12B | Reac. Prod. from Exp. XV[2] | WITCO 10-410 | Reac. Prod. 18[2,3] |
| Actives | 62% | 63.1% | 60% | 56% |
| Free oil | 15% | 20.3% | | 15.6% |
| Water | 19.5% | 14.4% | | 25.4% |
| Na Sulfate | 3.5% | 2.2% | | 3.0% |
| $\overline{\epsilon\omega}$ | 410 | 405 | 405 | 450 |

| Slug Formul.-Oil Recovery Data | | | | | | | |
|---|---|---|---|---|---|---|---|
| | Actives | NaCl | Co-Surfactant | Slug Pore Vol. | Core Size | Oil Source | O Recc |
| WITCO 12B Reac. Prod. | 3.0% | 1.5% | 0.0% | 0.05 | 1" × 1" × 1' | Glen Pool Crude | 42. |
| Exp. XV | 3.0% | 1.5% | 0.0% | 0.05 | 1" × 1" × 1' | Glen Pool Crude | 48. |
| WITCO 10-410 Reac. Prod. | 3.0% | 0.75%[4] | 0.84% Hexanol | 0.05 | 1" × 1" × 1' | Salem Crude | 19 |
| Exp. XV | 3.0% | 1.5% | 0.80% Hexanol Isoamyl | 0.05 | 1" × 1" × 1' | Salem Crude | 36 |
| WITCO 10-410 | 3.0% | 1.5% | 1.05% alcohol Isoamyl | 0.05 | 2" × 2" × 1' | Salem Crude | 41. |
| WITCO 10-410 Reac. Prod. | 3.0% | 1.5% | 1.05% alcohol Isoamyl | 0.05 | 2" × 2" × 1' | Salem Crude | 39. |
| Exp. XV | 3.0% | 1.5% | 2.95% alcohol | 0.05 | 2" × 2" × 1' | Salem Crude | 61. |

TABLE XVIII-continued

| | | | | | | | |
|---|---|---|---|---|---|---|---|
| ITCO 10-410 | 3.0% | 0.75%[4] | 0.84% Hexanol | 0.05 | 1" × 1" × 1' | Salem Crude | 19% |
| ITCO 10-410 | 3.0% | 0.75%[4] | 0.84% Hexanol | 0.05 | 2" × 2" × 1' | Salem Crude | 25.5% |
| ac. Prod. p. XV | 3.0% | 1.5% | 0.80% Hexanol | 0.05 | 1" × 1" × 1' | Salem Crude | 36.0% |
| ac. Prod. p. XV | 3.0% | 1.5% | 0.70% Hexanol | 0.05 | 2" × 2" × 2' | Salem Crude | 29.1% |
| ac. Prod. 18 | 3.0% | 1.5% | 0.45% Hexanol | 0.05 | 2" × 2" × 2' | Salem Crude | 41.0% |

The acidic reaction products were neutralized by addition of caustic and then extracted with a mixture of isopropyl alcohol and water substantially as set forth in Example XVI.

The oil feed stock for this product was a blend of about 67% of the oil feed stock from Example XV and about 33% of another oil feed stock characterized as having an average molecular weight of 480; an API gravity at 60° F. of 14.8; boiling range of 590°–1009° F.; and an aromatic content of about 62.3%. This blended feed stock was sulfonated substantially as set forth in Example XV.

ITCO 10-410 does not appear to be able to tolerate higher NaCl concentrations with hexanol.

As can be seen from the above tabulated results, the reaction products of the invention provide improved oil recovery in comparison with the tested mahogany sulfonates.

TABLE A

OIL FEED STOCK CHARACTERIZATIONS

| | Avg. mol. wt. | Gravity API at 60° F. | Viscosity, SSU 75° F. | Viscosity, SSU 110° F. | Viscosity, SSU 210° F. | Boiling Pt. Range F.° (corr.) | Pour Pt. °F. | % S | Aromatics % | Polar % | Sat. % | Aliphatic H: Aromatic |
|---|---|---|---|---|---|---|---|---|---|---|---|---|
| | 350 | — | GEL | — | — | 600–1000° | — | — | 56.5 | — | — | 13 |
| | 373 | 12.7 | — | — | 91 | — | 70° | 1.5–2 | 75 | — | — | — |
| | 330–340 | — | — | — | — | — | — | — | 75 | — | — | — |
| | — | — | — | — | — | — | — | — | 47.9 | — | — | 9.7 |
| | 435 | 17.2 | GEL | 2271 | 89 | 824–989° | — | 1.55 | 64.9 | — | 35.1 | — |
| I | 386 | 21.9 | — | 254 | 46.9 | 600–1100° | 90° | 2.64 | 47.2 | 37.3 | 15.5 | — |
| II | 409 | — | — | — | — | — | — | — | — | — | — | — |
| III | 303 | 20.0 | — | 950 | 70 | 980–1090° | — | — | 47.7 | — | 48.8 | — |
| | 283 | 5.7 | — | — | — | 484–947° | — | — | — | — | — | — |
| | 285 | 17.4 | — | 307 | 45 | 745–742° | — | — | 60.2 | — | 33.0 | — |
| IA | — | — | — | — | — | — | — | — | 47.9 | — | — | 9.7 |
| B | — | — | — | — | — | — | — | — | 59.7 | — | — | 12.8 |
| IIA | — | — | — | — | — | — | — | — | 59.7 | — | — | 12.8 |
| B | — | — | — | — | — | — | — | — | 47.9 | — | — | 9.7 |
| C | — | — | — | — | — | — | — | — | 59.7 | — | — | 12.8 |
| III | — | — | — | — | — | — | — | — | 59.7 | — | — | 12.8 |
| IV | 351 | 13.0 | — | — | 58.3 | — | — | — | 75.3 | 8.0 | 16.7 | — |
| V | 390 | 14.0 | — | — | — | 696–918° | — | — | 70% | — | — | — |
| VI | 390 | 14.0 | — | — | — | 696–918° | — | — | 70% | — | — | — |
| VII | 390 | 14.0 | — | — | — | 696–918° | — | — | 70% | — | — | — |
| VIII A | 390 | 14.0 | — | — | — | 696–918° | — | — | 70% | — | — | — |

TABLE B

ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| 1-1 | — | 254°–348° | $H-C=O$, $-C-O-H$, $-C-O-C-$, $-C(=O)-O-R$ | — | C$_8$ oxo bottoms |
| 2 | 410 | — | $-C-OH$, $-C-O-C-$ | 24 | Polyalkoxy Tallow Alcohol (3.5 Mols of E. o) |
| 3 | 182 | — | $-C-O-H$, $-C-O-C-$ | 10 | Polyalkoxy Phenol (2 Mols of E. o) |
| 4 | 182 | — | $-C-O-H$, $-C-O-C-$ | 10 | Polyalkoxy Phenol (2 Mols of E. o) |

TABLE B-continued

ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| 5 | — | 254°–348° | H—C=O, —C—O—H, —C—O—C—, —C(=O)—O—R | — | C$_8$ oxo bottoms |
| 6 | 134 | 195° | —C—O—H, —C—O—C— | 6 | Diethylene Glycol Monoethyl Ether |
| 7 | 380 | — | —C—O—H, —C—O—C— | 14 | Polyalkoxy Nonylphenol (4 Mols of E. o) |
| 8 | 380 | — | —C—O—H, —C—O—C— | 14 | Polyalkoxy Nonylphenol (4 Mols of E. o) |
| 9 | 380 | — | —C—O—H, —C—O—C— | 14 | Polyalkoxy Nonylphenol (4 Mols of E. o) |
| 10 | 134 | 195° | —C—O—H, —C—O—C— | 6 | Diethylene Glycol Monoethyl Ether |
| 11 | 134 | 195° | —C—O—H, —C—O—C— | 6 | Diethylene Glycol Monoethyl Ether |
| 12 | — | 254°–348° | H—C=O, —C—O—H, —C—O—C—, —C(=O)—O—R | — | C$_8$ oxo bottoms |
| II-1 | — | 254°–348° | H—C=O, —C—O—H, —C—O—C—, —C(=O)—O—R | — | C$_8$ oxo bottoms |
| 2 | 118 | 171° | —C—O—H, —C—O—C— | 6 | 2-Butoxy Ethanol |
| 3 | 176 | 218° | —C—O—C—, —C(=O)—O—R | 8 | Acetate ester of diethylene glycol monoethyl ester |
| 4 | 144 | 194°–229° | —C—O—H | 9 | Octyl and Decyl Alcohols (50:50) |

TABLE B-continued
ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| 5 | 152 | 193°–229° | $-\underset{\mid}{\overset{\mid}{C}}-O-H, -\underset{\mid\mid}{\overset{\mid}{C}}-O-R$ (with $=O$) | 10 | 30% Octyl Alc., 30% Decyl Alc., 20% Me. caprylate, 20% Me. caprate |
| III-1 | 165 | 193°–224° | $-\underset{\mid\mid}{C}-O-R$ (C=O) | 11 | Me. Octoate and Me. Decanate (50:50) |
| 2 | 298 | 340° | $-\underset{\mid\mid}{C}-O-R$ (C=O) | 19 | Isopropyl Palmitate |
| 3 | 298 | 415°–442° | $-\underset{\mid\mid}{C}-O-R$ (C=O) | 15 | Me. Stearate and Me. Palmitate (50:50) |
| 4 | | | | | Butoxy ethyl acetate |
| 5 | 160 | 239°–270° | $-\underset{\mid\mid}{C}-O-H$ (C=O) | 9 | Octanoic Acid and Decanoic Acid (50:50) |
| 6 | 288 | — | $-C=C-$ | 21 | Pentadecylbenzene |
| 7 | — | 154°–202° | $-C=C-$ | — | Stoddard Solvent |
| 8 | 166 | 121° | $-C=C-$ | 2 | Perchloroethylene |
| 9 | 235 | — | $-C=C-$ | 18 | Dodecylbenzene |
| 10 | 258 | 390° | $-\underset{\mid\mid}{C}-O-H$ (C=O) | 16 | Palmitic Acid |
| 11 | 196 | 232° | $-C=C-$ | 14 | Tetradecene-1 |
| 12 | 252 | 320° | $-C=C-$ | 18 | Octadecene-1 |
| 13 | — | — | — | — | — |
| 14 | 98 | 129° | $-C=O, -C=C-$ | 6 | Mesityl Oxide |
| 15 | 176 | 218° | $-\underset{\mid}{\overset{\mid}{C}}-O-\underset{\mid}{\overset{\mid}{C}}-, -\underset{\mid\mid}{\overset{\mid}{C}}-O-R$ (C=O) | 8 | Acetate Ester of Diethylene Glycol Monoethyl Ether |
| 16 | 98 | 129° | $-C=O, -C=C-$ | 6 | Mesityl Oxide |
| 17 | 180 | 208° | $-C=C-$ | 6 | Trichlorobenzene |
| IV-1 | 196 | 232° | $-C=C-$ | 14 | Tetradecene-1 |
| 2 | — | — | — | — | — |

TABLE B-continued

ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| V-1 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| 2 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| 3 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| VI-1 | — | — | — | — | — |
| 2 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| 3 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| 4 | — | 254°–348° | $H-C=O, -\overset{|}{\underset{|}{C}}-O-H, -\overset{|}{\underset{|}{C}}-O-\overset{|}{\underset{|}{C}}-, -\underset{\underset{O}{\|}}{C}-O-R$ | — | C$_8$ oxo bottoms |
| VII-1 | — | 254°–348° | $H-C=O, -\overset{|}{\underset{|}{C}}-O-H, -\overset{|}{\underset{|}{C}}-O-\overset{|}{\underset{|}{C}}- -\underset{\underset{O}{\|}}{C}-O-R$ | — | C$_8$ oxo bottoms |
| VIII | — | 254°–348° | $H-C=O, -\overset{|}{\underset{|}{C}}-O-H, -\overset{|}{\underset{|}{C}}-O-\overset{|}{\underset{|}{C}}- -\underset{\underset{O}{\|}}{C}-O-R$ | — | C$_8$ oxo bottoms |

TABLE B-continued

ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| IX | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-$ $-\underset{\underset{O}{\|}}{C}-O-R$ | — | C$_8$ oxo bottoms |
| X-A | — | — | — | — | — |
| B | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-$ $-\underset{\underset{O}{\|}}{C}-O-R$ | — | C$_8$ oxo bottoms |
| XI-A | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-$ $-\underset{\underset{O}{\|}}{C}-O-R$ | — | C$_8$ oxo bottoms |
| B | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-$ $-\underset{\underset{O}{\|}}{C}-O-R$ | — | C$_8$ oxo bottoms |
| XII-A | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-,$ $-\underset{\underset{O}{\|}}{C}-O-R$ | — | C$_8$ oxo bottoms |
| B | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-,$ $-\underset{\underset{O}{\|}}{C}-O-R$ | — | C$_8$ oxo bottoms |
| C | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-,$ $-\underset{\underset{O}{\|}}{C}-O-R$ | — | C$_8$ oxo bottoms |
| XIII-A | — | — | — | — | — |
| B | — | 254°–348° | $H-\overset{\|}{C}=O, -\overset{\|}{\underset{\|}{C}}-O-H, -\overset{\|}{\underset{\|}{C}}-O-\overset{\|}{\underset{\|}{C}}-,$ | — | C$_8$ oxo bottoms |

TABLE B-continued

ADDITIVES CHARACTERIZATIONS

| Ex. | Avg. mol. wt. | Boiling Pt. Range, °C. | Reactive Moiety | Avg. C Chain | Chemical Name |
|---|---|---|---|---|---|
| XIV | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_8$ oxo bottoms |
| XV | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |
| XVI | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |
| XVII-A | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |
| B | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |
| XVIII-A | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |
| B | — | 254°–348° | $-\underset{\underset{O}{\parallel}}{C}-O-R$, $H-C=O$, $-\underset{\mid}{C}-O-H$, $-\underset{\mid}{C}-O-\underset{\mid}{C}-$, | — | $C_{10}$ oxo bottoms |

TABLE C

SULFONATION PRODUCT CHARACTERIZATION

| Product of Examples | Total Sulfonate | Mono-sulfonate | Poly-sulfonate | Unmodified Oil | $\epsilon\omega$ |
|---|---|---|---|---|---|
| I-2 | — | 39.2% | — | — | 430 |
| -8 | — | 28.5% | — | 57.3 | 395 |
| -9 | 34.9% | 30.1% | 4.8% | 58.0 | 423 |
| -11 | 59.5% | 31.8% | 27.7% | 52.7 | 400 |
| -12 | 42.2% | 33.5% | 8.7% | 51.9 | 411 |
| II-6 | 33.4% | 30.2% | 3.2% | — | 430 |
| -7 | 34.4% | 25.1% | 11.3% | — | 412 |
| -9 | — | 28.8% | — | 48.6 | — |
| -10 | 25.3% | 24.0% | 1.3% | 56.9 | 459 |
| III-1 | — | 48.2% | — | 57.3 | 506 |
| -2 | — | 55.4% | — | 39.2 | 432 |
| -3 | — | 55.2% | — | 36.2 | 432 |
| -4 | — | 20.0% | — | 83.0 | 432 |
| -5 | — | 58.1% | — | 37.0 | 432 |
| -6 | — | 46.8% | — | 47.1 | 432 |
| -7 | — | 32.3% | — | 68.0 | 432 |
| -8 | — | 40.5% | — | 59.2 | 432 |
| -9 | — | 43.5% | — | 42.8 | 432 |
| -10 | — | 56.7% | — | 44.0 | 432 |
| -11 | — | 45.9% | — | 52.0 | 432 |
| -12 | — | 46.0% | — | 45.5 | 432 |
| -13 | — | — | — | — | — |
| -14 | — | 17.0% | — | 83.5 | 432 |
| -15 | — | 47.7% | — | 41.2 | 432 |
| -16 | — | 37.2% | — | 52.0 | 432 |
| -17 | — | 37.0% | — | 60.0 | 432 |
| IV | — | 21.4% | — | 71.8 | 507 |
| V-1 | — | 40.0% | — | 57.1 | 532 |
| -2 | — | 51.5% | — | 42.5 | 532 |
| -3 | — | 50.1% | — | 48.5 | 532 |
| VI-1 | — | — | — | — | 483 |
| -2 | — | 45.0% | — | 54.4 | 483 |
| -3 | — | 45.0% | — | 55.8 | 483 |
| -4 | — | 40.5% | 20.8 | 35.7 | 483 |
| VII | — | — | — | — | — |
| VIII | — | 31.2% | — | 70.8 | 400 |
| IX | — | — | — | 63.6 | — |
| X | — | 43.1% | — | 56.9 | — |
| XI-1 | — | 14.3% | 16.3 | 55.8 | 507 |
| -2 | — | — | — | — | — |
| XII-1 | — | — | — | — | — |
| -2 | — | 12.0% | — | — | 506 |
| -3 | — | 18.5% | — | — | — |
| XIII-1 | 16.8 | 7.8% | — | | 501 |
| -2 | 19.6 | 13.0% | — | | 574 |
| XIV | — | 39.3% | — | — | — |
| XV-1 | — | 40.0% | — | — | — |
| -2 | — | 40.0% | — | — | — |
| XVI | — | 65.0% | — | — | 438 |
| XVII | | 33.4–41.0% | — | — | 438 |
| XVIII | | | | | |

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth in the hereto-appended claims.

We claim as our invention:

1. A sulfonated petroleum composition which is substantially homogeneous under reaction conditions utilized to produce said composition, and comprising on a 100 organic weight percent total weight basis
    (A) from about 5 to 98 weight percent of monosulfonated hydrocarbon,
    (B) from about 0 to 50 weight percent of polysulfonated hydrocarbon, and
    (C) from about 2 to 90 weight percent of non-sulfonated petroleum,
said composition having been prepared by contacting a liquid hydrocarbon mixture with a gaseous sulfur trioxide composition at a temperature of from about 77° to 392° F., said hydrocarbon mixture comprising initially on a 100 weight percent total weight basis
    (A) from about 85 to 99.5 weight percent of a petroleum oil feed stock, and
    (B) from about 0.5 to 15 weight percent of an additive, said petroleum oil feed stock being characterized by
        ($a_1$) having an API gravity ranging from about 5° to 60° at 60° F.,
        ($a_2$) having a boiling point (corrected atmospheric) ranging from about −20° to 1400° F., and
        ($a_3$) containing from about 10 to 95 weight percent (100 weight percent total basis) sulfonatable components,
    said additive being characterized by
        ($b_1$) being comprised of unsulfonatable organic radical portions possessing an average molecular weight range from about 55 to 6000,
        ($b_2$) having a boiling point in the range from about 212° to 932° F. corrected atmospheric, and
        ($b_3$) a preponderance of such radicals each having attached at least one proton replaceable by a sulfo group and at least one moiety selected from the group consisting of an aromatic nucleus, an olefinic carbon pair, and an oxygen atom directly bonded to a carbon atom by at least one bond.

2. A sulfonated petroleum composition as defined in claim 1 wherein said additive includes at least one $C_2$ to $C_{30}$ main hydrocarbon chain and is characterized as having a boiling point in the range of about 212° to 932° F.

3. A sulfonated petroleum composition as defined in claim 1 wherein said additive is a $C_4$ to $C_{28}$ oxygen-containing compound characterized as having a boiling point in the range of about 212° to 932° F.

4. A sulfonated petroleum composition as defined in claim 3 wherein said oxygen-containing compound is a hydroxy-containing compounds.

5. A sulfonated petroleum composition as defined in claim 3 wherein said oxygen-containing compound is an oxo alcohol still bottom.

6. A sulfonated petroleum composition as defined in claim 5 wherein said oxo alcohol still bottom is comprised of about 2 to 20% by weight of octyl alcohol, about 4 to 40% by weight of nonyl alcohol, about 25 to 90% by weight of decyl and higher boiling materials and about 20 to 80% by weight of esters.

7. A sulfonated petroleum composition as defined in claim 5 wherein said oxo alcohol still bottom is comprised of about 5% by weight of octyl alcohol, about 10% by weight of nonyl alcohol, about 35% by weight of decyl and higher boiling materials, about 45% by weight of esters and about 5% by weight of soaps.

8. A sulfonated petroleum composition as defined in claim 1 wherein said additive is selected from the group consisting of oxo alcohol still bottoms, $C_4$ to $C_{28}$ aliphatic alcohols, alkoxylated phenols, diethylene glycol monoethyl ether, alkoxylated nonyl phenols, alkoxylated tallow alcohol, 2-butoxy ethanol, acetate ester of diethylene glycol monoethyl ether, $C_8$–$C_{10}$ alcohols, $C_8$–$C_{10}$ fatty acid methyl esters, isopropyl palmitate, hydrogenated $C_{12}$–$C_{16}$ fatty acid methyl esters, acetate ester of ethylene glycol monobutyl ether, $C_8$ to $C_{10}$ fatty acids, branched chain $C_{15}$ alkyl benzene, branched chain dodecylbenzenes, palmitic acid, $C_{14}$-$C_{18}$ α-olefins, mesityl oxide, acetate ester of ethylene glycol monoethyl ether, and mixtures thereof.

9. A sulfonated petroleum composition as defined in claim 1 wherein said petroleum oil feed stocks include aromatic portions which have a molecular weight in the range of about 200 through about 1000.

10. A sulfonated petroleum composition as defined in claim 1 wherein said additive is selected from the group consisting of unsaturated aliphatic hydrocarbon compounds, substituted and unsubstituted aromatic compounds, olefinic compounds, oxygen-containing compounds, hydroxy-containing compounds, ester compounds, ether compounds, ester-ether compounds, ketone compounds, fatty acid compounds and mixtures thereof.

11. A sulfonated petroleum composition as defined in claim 4 wherein said hydroxy-containing compound is a $C_6$ to $C_{28}$ alcohol.

12. A sulfonated petroleum composition as defined in claim 11 wherein said alcohol is selected from the group consisting of hexanol, octanol, nonanol, decanol, octadecanol, dodecanol, lauryl, myristyl, palmityl, stearyl, and mixtures thereof.

13. A sulfonated petroleum composition as defined in claim 3 wherein said oxygen-containing compound is a phenolic compound.

14. A sulfonated petroleum composition as defined in claim 13 wherein said phenolic compound is selected from the group consisting of phenol, $C_1$ to $C_{16}$ alkyl phenols, $C_1$ to $C_{16}$ alkyl $C_1$ to $C_{200}$ alkoxy phenols and mixtures thereof.

15. A sulfonated petroleum composition as defined in claim 3 wherein said oxygen-containing compound is a glycol compound.

16. A sulfonated petroleum composition as defined in claim 3 wherein said oxygen-containing compound is alkoxylated with about 1 to 200 moles of a $C_2$ to $C_4$ alkylene oxide per mole of oxygen-containing compound.

17. A sulfonated petroleum composition as defined in claim 3 wherein said oxygen-containing compound is tallow alcohol.

18. A sulfonated petroleum composition as defined in claim 1 wherein said additive is a $C_4$ to $C_{40}$ olefinic hydrocarbon characterized as having a boiling point in the range of about 212° to 932° F.

19. A sulfonated petroleum composition as defined in claim 1 wherein said additive is a $C_6$ to $C_{40}$ aromatic compound characterized as having a boiling point in the range of about 212° to 932° F.

20. A sulfonated petroleum composition as defined in claim 1 wherein said additive is a $C_4$ to $C_6$ ether characterized as having a boiling point in the range of about 212° to 932° F.

21. A sulfonated petroleum composition as defined in claim 20 wherein said ether is selected from the group consisting of 4-methoxy butanol, 2-ethoxy ethanol, 2-propoxy ethanol, 2-butoxy ethanol, diethylene glycol, diethylene glycol monoethyl ether, diethylene glycol butyl ether and mixtures thereof.

22. A sulfonated petroleum composition as defined in claim 1 wherein said additive is a $C_4$ to $C_6$ hydrocarbon ether ester characterized as having a boiling point in the range of about 212° to 932° F.

23. A sulfonated petroleum composition as defined in claim 1 wherein said ether ester is selected from the group consisting of acetate ester of diethylene glycol monoethyl ether, acetate ester of ethylene glycol monoethyl ether, acetate ester of butylene glycol monoethyl ether and mixtures thereof.

24. A sulfonated petroleum composition as defined in claim 1 wherein the additive is a $C_7$ to $C_{30}$ alkaryl compound characterized as having a boiling point in the range of about 212° to 932° F.

25. A sulfonated petroleum composition as defined in claim 1 wherein said additive is a $C_1$ to $C_4$ alkyl ester of a $C_6$ to $C_{20}$ aliphatic acid characterized as having a boiling point in the range of about 212° to 932° F.

26. A sulfonated petroleum composition as defined in claim 25 wherein said alkyl ester acid is a methyl ester of a $C_{12}$ to $C_{18}$ fatty acid.

27. A sulfonated petroleum composition as defined in claim 25 wherein said alkyl ester acid is a methyl ester of a $C_8$ to $C_{10}$ fatty acid.

28. A sulfonated petroleum composition is defined in claim 25 wherein said alkyl ester acid is a methyl ester of a $C_{14}$ to $C_{28}$ fatty acid.

29. A sulfonated petroleum composition as defined in claim 1 wherein said additive is a $C_6$ to $C_{28}$ alkyl ester of a $C_6$ to $C_{28}$ aliphatic alcohol characterized as having a boiling point in the range of about 212° to 932° F.

30. A sulfonated petroleum composition as defined in claim 1 wherein said petroleum oil feed stock is selected from the group consisting of crude oil, topped crude oil and mixtures thereof.

31. A sulfonated petroleum composition as defined in claim 1 wherein said amount of additive in said mixture ranges from about 0.5% to about 5.0% by weight of said petroleum oil feed stock.

32. A sulfonated petroleum composition as defined in claim 1 wherein said amount of additive in said mixture ranges from about 2% to about 10% by weight of said petroleum oil feed stock.

33. A sulfonated petroleum composition as defined in claim 1 wherein said petroleum composition comprises petroleum sulfonates having an average equivalent weight of from about 350 to about 550.

34. A sulfonated petroleum composition as defined in claim 1 wherein said petroleum composition is neutralized with a sufficient amount of an alkali to attain a composition having a pH in the range of about 3 to 12.

35. A sulfonated petroleum composition as defined in claim 1 wherein said petroleum composition is neutralized with a sufficient amount of an alkali to attain a composition having a pH in the range of about 6 to 10.

36. A sulfonated petroleum composition which is substantially homogeneous under reaction conditions utilized to produce said compositions, and comprising on a 100 organic weight percent total weight basis
  (A) from about 5 to 98 weight percent of monosulfonated hydrocarbon,
  (B) from about 0 to 50 weight percent of polysulfonated hydrocarbon, and
  (C) from about 2 to 90 weight percent of nonsulfonated petroleum,
said composition having been prepared by contacting a liquid hydrocarbon mixture with a gaseous sulfur trioxide composition at a temperature of from about 77° to 392° F., said hydrocarbon mixture comprising initially on a 100 weight percent total weight basis
  (a) from about 85 to 99.5 weight percent of a petroleum oil feed stock, and (b) from about 0.5 to 15 weight percent of an additive, said petroleum oil feed stock being characterized by
- ($a_1$) having an API gravity ranging from about 5° to 60° at 60° F.,
- ($a_2$) having a boiling point (corrected atmospheric) ranging from about −20° to 1400° F., and
- ($a_3$) containing from about 10 to 95 weight percent (100 weight percent total basis) sulfonatable components, said additive being characterized by
- ($b_1$) being comprised of unsulfonatable organic radical portions possessing an average molecular weight range from about 55 to 6000,
- ($b_2$) having a boiling point in the range from about 212° to 932° F. corrected atmospheric, and
- ($b_3$) a preponderance of such radicals each having attached at least one proton replaceable by a sulfo group and at least one aromatic nucleus directly bonded to a carbon atom by at least one bond.

37. A sulfonated petroleum composition which is substantially homogeneous under reaction conditions utilized to produce said compositions, and comprising on an 100 organic weight percent total weight basis
   (A) from about 5 to 98 weight percent of monosulfonated hydrocarbon,
   (B) from about 0 to 50 weight percent of polysulfonated hydrocarbon, and
   (C) from about 2 to 90 weight percent of non-sulfonated petroleum,
said composition having been prepared by contacting a liquid hydrocarbon mixture with a gaseous sulfur trioxide composition at a temperature of from about 77° to 392° F., said hydrocarbon mixture comprising initially on a 100 weight percent total weight basis
   (a) from about 85 to 99.5 weight percent of a petroleum oil feed stock, and
   (b) from about 0.5 to 15 weight percent of an additive, said petroleum oil feed stock being characterized by
   - ($a_1$) having an API gravity ranging from about 5° to 60° at 60° F.,
   - ($a_2$) having a boiling point (corrected atmospheric) ranging from about −20° to 1400° F., and
   - ($a_3$) containing from about 10 to 95 weight percent (100 weight percent total basis) sulfonatable components,
said additive being characterized by
   - ($b_1$) being comprised of unsulfonatable organic radical portions possessing an average molecular weight range from about 55 to 6000,
   - ($b_2$) having a boiling point in the range from about 212° to 932° F., corrected atmospheric, and
   - ($b_3$) a preponderance of such radicals each having attached at least one proton replaceable by a sulfo group and at least one olefinic carbon pair directly bonded to a carbon atom by at least one bond.

38. A sulfonated petroleum composition which is substantially homogeneous under reaction conditions utilized to produce said composition, and comprising on a 100 organic weight percent total weight basis
   (A) from about 5 to 98 weight percent of monosulfonated hydrocarbon,
   (B) from about 0 to 50 weight percent of polysulfonated hydrocarbon, and
   (C) from about 2 to 90 weight percent of non-sulfonated petroleum,
said composition having been prepared by contacting a liquid hydrocarbon mixture with a gaseous sulfur trioxide at a temperature of from about 77° to 392° F., said hydrocarbon mixture comprising initially on a 100 weight percent total weight basis
   (a) from about 85 to 99.5 weight percent of a petroleum oil feed stock, and
   (b) from about 0.5 to 15 weight percent of an additive, said petroleum oil feed stock being characterized by
   - ($a_1$) having an API gravity ranging from about 5° to 60° at 60° F.,
   - ($a_2$) having a boiling point (corrected atmospheric) ranging from about −20° to 1400° F., and
   - ($a_3$) containing from about 10 to 95 weight percent (100 weight percent total basis) sulfonatable components,
said additive being characterized by
   - ($b_1$) being comprised of unsulfonatable organic radical portions possessing an average molecular weight range from about 55 to 6000,
   - ($b_2$) having a boiling point in the range from about 212° to 932° F. corrected atmospheric, and
   - ($b_3$) a preponderance of such radicals each having attached at least one proton replaceable by a sulfo group and at least one oxygen atom directly bonded to a carbon atom by at least one bond.

39. A sulfonated petroleum composition as defined in claim 42 wherein said composition is subjected to a deoiling process comprising admixing said sulfonated petroleum composition with a hydrophilic solvent selected from the group consisting of water, a $C_1$–$C_5$ alcohol and semipolar organic compounds so that a phase separation occurs and any unsulfonated oil is removed to attain a deoiled sulfonated petroleum composition.

40. A sulfonated petroleum composition as defined in claim 39 wherein said deoiled petroleum composition is neutralized with a sufficient amount of an alkali to attain a composition having a pH in the range of about 3 to 12.

41. A substantially homogeneous sulfonated petroleum composition as defined in claim 40 wherein any precipitated salt formed during neutralization is removed from said petroleum composition.

42. A sulfonated petroleum composition as defined in claim 34 wherein said neutralized sulfonated petroleum composition is subjected to a deoiling process comprising admixing said neutralized petroleum composition with a hydrophilic solvent selected from the group consisting of water, a $C_1$–$C_5$ alcohol and semipolar organic compounds so that a phase separation occurs and any unsulfonated oil is removed to attain a neutralized deoiled sulfonated petroleum composition.

* * * * *